(12) United States Patent
Fong et al.

(10) Patent No.: US 7,964,248 B2
(45) Date of Patent: Jun. 21, 2011

(54) DUAL PHOTOINITIATOR, PHOTOCURABLE COMPOSITION, USE THEREOF AND PROCESS FOR PRODUCING A THREE DIMENSIONAL ARTICLE

(75) Inventors: John Wai Fong, Temple City, CA (US); Carole Chapelat, Saint Louis (FR); Loic Messe, Riedisheim (FR); Ranjana Patel, Little Hallingbury (GB); Laurence Messe, Riedisheim (FR)

(73) Assignee: Huntsman Advanced Materials Americas LLC, The Woodlands, TX (US)

( * ) Notice: Subject to any disclaimer, the term of this patent is extended or adjusted under 35 U.S.C. 154(b) by 0 days.

(21) Appl. No.: 12/595,643

(22) PCT Filed: Apr. 9, 2008

(86) PCT No.: PCT/US2008/059708
§ 371 (c)(1),
(2), (4) Date: Mar. 23, 2010

(87) PCT Pub. No.: WO2008/127930
PCT Pub. Date: Oct. 23, 2008

(65) Prior Publication Data
US 2010/0327493 A1  Dec. 30, 2010

Related U.S. Application Data

(60) Provisional application No. 60/923,356, filed on Apr. 13, 2007.

(51) Int. Cl.
G03F 7/038 (2006.01)
G03F 7/00 (2006.01)
G03C 5/00 (2006.01)
B05D 1/00 (2006.01)

(52) U.S. Cl. .......... 427/466; 427/510; 430/269; 522/15; 522/25; 522/31

(58) Field of Classification Search .......... 430/269; 522/15, 25, 31, 168, 129, 170; 427/466, 427/510
See application file for complete search history.

(56) References Cited

U.S. PATENT DOCUMENTS

| | | | |
|---|---|---|---|
| 4,090,936 A * | 5/1978 | Barton | 430/280.1 |
| 4,287,228 A * | 9/1981 | Schlesinger | 427/514 |
| 5,943,235 A | 8/1999 | Earl et al. | |
| 6,054,250 A * | 4/2000 | Sitzmann et al. | 430/280.1 |
| 6,350,792 B1 * | 2/2002 | Smetana et al. | 522/81 |
| 7,579,390 B2 * | 8/2009 | Ushirogouchi et al. | 523/160 |
| 7,604,343 B2 * | 10/2009 | Ishikawa | 347/102 |
| 7,858,670 B2 * | 12/2010 | Akiyama et al. | 522/83 |
| 2006/0021537 A1 | 2/2006 | Ohtsu et al. | |
| 2006/0251901 A1 * | 11/2006 | Armstrong et al. | 428/413 |
| 2007/0267134 A1 * | 11/2007 | Konarski et al. | 156/273.3 |
| 2008/0045618 A1 * | 2/2008 | Nagvekar | 522/27 |

FOREIGN PATENT DOCUMENTS

| | | |
|---|---|---|
| DE | 19500968 | 7/1996 |
| EP | 1621260 | 2/2006 |
| WO | WO 2007/031505 * | 3/2007 |

* cited by examiner

*Primary Examiner* — Susan W Berman

(57) ABSTRACT

The present invention is directed to a photoinitiator composition comprising two different cationic photoinitiators and a photocurable composition comprising said photoinitiator composition. Moreover, the present invention relates to the use of the photoinitiator composition and the photocurable composition. Furthermore, the present invention relates to a process for producing a three dimensional article.

30 Claims, No Drawings

DUAL PHOTOINITIATOR, PHOTOCURABLE COMPOSITION, USE THEREOF AND PROCESS FOR PRODUCING A THREE DIMENSIONAL ARTICLE

CROSS REFERENCE TO RELATED APPLICATIONS

This application is the National Phase of International Application PCT/US2008/059708 filed Apr. 9, 2008 which designated the U.S. and which claims priority to U.S. Patent Application 60/923,356 filed Apr. 13, 2007. The noted applications are incorporated herein by reference.

FIELD OF THE INVENTION

The present invention is directed to a photoinitiator composition comprising two different cationic photoinitiators and a photocurable composition comprising said photoinitiator composition. Moreover, the present invention relates to the use of the photoinitiator composition and the photocurable composition. Furthermore, the present invention relates to a process for producing a three dimensional article.

BACKGROUND OF THE INVENTION

Photocurable resins are of continuing interest because they are regarded as 'green' solutions, neither requiring solvents nor, if containing water, energy intensive water drying resources. Within this area, it is of growing interest to provide stable photo curable resin compositions which after cure at high speed, result in cured materials with high toughness and increased thermal properties. Such desired properties are particularly sought in three dimensional printing applications.

Liquid-based solid imaging, for example, stereolithography, is a process whereby a photoformable liquid is applied as a thin layer to a surface and exposed to actinic radiation such that the liquid solidifies. Subsequently, new thin layers of photoformable liquids are coated onto previous layers of liquid or previously solidified sections. The new layers are then exposed imagewise in order to solidify portions imagewise and in order to induce adhesion between portions of the new hardened region and portions of the previously hardened region. Each imagewise exposure is of a shape that relates to a pertinent cross-section of a photohardened object such that when all the layers have been coated and all the exposures have been completed, an integral photohardened object can be removed from the surrounding liquid composition.

Initiation of polymerisation in a monomer, oligomer or prepolymer may be effected in a number of ways. One such way is by irradiation, for example with ultraviolet radiation, in which case it is normally necessary that the polymerisable composition should contain an initiator, commonly referred to as a "photoinitiator". There are two main types of curing chemistry which can be used in this process: free radical and cationic. Although cationic curing has many advantages, its disadvantages, particularly with regard to the photoinitiators used, leads it to be used only in a minority of applications. Most frequently used cationic initiators are either organic iodonium or sulfonium salts.

Photocurable compositions used in the art tend to be thermally instable. The viscosity of photocurable compositions used in the art rises over time, even in absence of UV light, due to thermal decomposition of the photoinitiator. Great efforts are undertaken to stabilise the resins.

Reactive cationic photoinitiators are particularly responsible for viscosity instability in the bath of resin even at 25 to 30° C. or, more especially, if used at elevated temperatures. From the very process of stereolithography, the resin is regularly subjected to low levels of UV-irradiations that triggers photodecomposition of the photoinitiator and produces small amounts of active species. Cationic photoinitiator containing hexafluoroantimony salt or iodonium salts are especially known to be prone to instability, due to their high reactivity. Several attempts have been made to stabilise the formulations by adding various types of low basicity compounds.

U.S. Pat. No. 6,099,787 discloses a process for the production of three-dimensional articles by stereolithography comprising polymerizing of a radiation curable composition comprising a mixture of a cationically curable compound and a free radically curable compound and at least one photoinitiator for polymerization; here, benzyl-N,N-dimethylamine is brought into contact with the composition at a concentration of 5 to 5000 ppm to delay or prevent a significant increase in viscosity of the overall composition.

WO 03/104296 A1 describes an actinic radiation curable composition comprising at least one actinic radiation curable cationically polymerizable compound, at least one cationic photoinitiator and at least one stabilizer which is a complex of a Lewis acid and a Lewis base. The stabilizer is added to the photocurable composition in order to improve storage stability.

U.S. Pat. No. 5,665,792 discloses stabilizers for photo hardenable epoxy composition which have limited solubility in the composition and a density which is different from that of the composition, and which are salts of a group IA or group IIA metal ion and a weak acid, the weak acid having a pKa in water of greater than 3.0.

There is thus a need to further increase the viscosity stability of photocurable liquid compositions. The problems associated with the stabilizer presently known to improve viscosity and thermal stability are that they are consumed to avoid the resin ageing. When the stabilizer is totally consumed, the resin viscosity drastically increases and becomes too high for convenient use. Furthermore, amine stabilizers such as benzyl N,N-dimethylamine decrease the speed of the photocuring process since the amine is basic and consumes the photo acid generated by the cationic photoinitiator during irradiation. By consuming the active species the speed of the photocuring process of the resin is decreased. For that reason only small amounts of amine stabilizer can be added with the consequence that the efficiency is limited.

Cationic photoinitiators containing sulfonium hexafluorophosphate salts are considered to be more stable over time. However, the sulfonium hexafluorophosphate salts are less reactive which reduces the speed of the photocuring process.

WO 00/63272 A1, WO 03/093901 A1, US 2006/0231982 A1 and EP 0 848 294 A1 disclose photocurable resin compositions used for photo fabrication of three dimensional objects which comprise at least one cationic photoinitiator.

SUMMARY OF THE INVENTION

The present invention relates to a photoinitiator composition comprising at least two cationic photoinitiators of differing thermal stability in radiation curable compositions. This provides an advantageous compromise of thermal stability of the liquid composition and mechanical performance of the cured resin.

It is an object of the present invention to provide a photoinitiator composition which overcomes the problem associated with the photocurable compositions disclosed in the prior art. The photoinitiator composition according to the present invention improves the thermal stability of photocurable compositions without the need of stabilizers. Furthermore, viscosity stabilization is achieved without loss of reactivity of the liquid resin or loss in performances of the final parts. Thus, the present photoinitiator composition provides a photocurable compositions which demonstrate an advantageous compromise of reactivity and thermal stability.

DETAILED DESCRIPTION OF THE INVENTION

Both aforementioned aspects (thermal instability and desired improvement of mechanical properties) may be improved via the formulations described in this disclosure. The photoinitiator composition disclosed herein comprises (a) at least one cationic photoinitiator (A) selected from the group consisting of sulfonium salts wherein the anion is a fluorophosphate defined by the following formula (I):

(b)  $PF_nR^x{}_{6-n}{}^{\ominus}$     (I)

(c) with n an integer from 1 to 6 and
(d)=substituted or unsubstituted $C_{1-6}$-alkyl or substituted or unsubstituted aryl or heteroaryl; and
(e) at least one cationic photoinitiator (B) which is different from (A).

The weight ratio of (A) to (B) is higher than 0.1.

Preferably the weight ratio of (A) to (B) is higher than 0.2, preferably higher than 0.5, more preferably higher than 1, most preferably higher than 2, in particular higher than 5.

According to a preferred embodiment of the present invention the weight ratio of (A) to (B) is between 0.1 and 15, preferably between 0.3 and 15, more preferably between 0.8 and 12, most preferably between 1 and 8, in particular between 2 and 10, for example between 5 and 10.

In the above mentioned formula (I) n is an integer from 1 to 6, preferably an integer from 4 to 6, most preferably n is 6, i.e. hexafluorophosphate ($PF_6{}^{\ominus}$).

$R^x$ in the above mentioned formula (I) is preferably unsubstituted $C_{1-6}$-alkyl selected from methyl, ethyl, propyl, isopropyl; or unsubstituted aryl selected from phenyl or naphthyl; or substituted aryl selected from halogenated aryl preferably fluorinated and/or chlorinated aryl groups, in particular pentafluorophenyl, pentachlorophenyl, tetrafluorophenyl or tetrachlorophenyl.

Cationic Photoinitiator (A)

The cationic photoinitiator composition according to the present invention comprises at least one cationic photoinitiator (A) which is selected from the group consisting of sulfonium salts wherein the anion is a fluorophosphate defined by the following formula (I):

 $PF_nR^x{}_{6-n}{}^{\ominus}$     (I)

with n=an integer from 1 to 6 and
$R^x$=substituted or unsubstituted $C_{1-6}$-alkyl or substituted or unsubstituted aryl or heteroaryl, preferably $R^x$ is unsubstituted $C_{1-6}$-alkyl selected from methyl, ethyl, propyl, isopropyl; or unsubstituted aryl selected from phenyl or naphthyl; or substituted aryl selected from halogenated aryl preferably fluorinated and/or chlorinated aryl groups, in particular pentafluorophenyl, pentachlorophenyl, tetrafluorophenyl or tetrachlorophenyl. Preferably $R^x$ is aryl and n is an integer from 1 to 5.

Preferably the cationic photoinitiator (A) is a sulfonium hexafluorophosphate or a mixture of different sulfonium hexafluorophosphate(s).

Sulfonium salts within the meaning of the present invention are sulfonium salts or oxosulfonium salts.

According to a preferred embodiment of the present invention the cationic photoinitiator (A) is presented by the following formula (II)

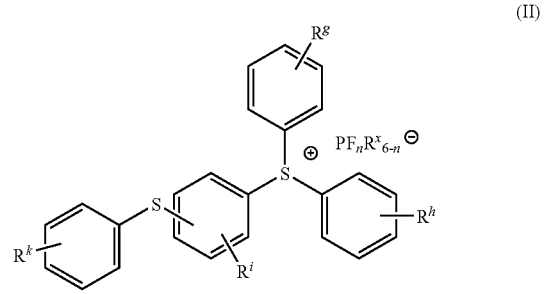

(II)

wherein n is an integer from 1 to 6 preferably an integer from 4 to 6, most preferably n is 6, i.e., hexafluorophosphate ($PF_6{}^{\ominus}$);

$R^x$ is substituted or unsubstituted $C_{1-6}$-alkyl; or substituted or unsubstituted aryl or heteroaryl, preferably $R^x$ is unsubstituted $C_{1-6}$-alkyl selected from methyl, ethyl, propyl, isopropyl; or unsubstituted aryl selected from phenyl or naphthyl; or substituted aryl selected from halogenated aryl preferably fluorinated and/or chlorinated aryl groups, in particular pentafluorophenyl, pentachlorophenyl, tetrafluorophenyl or tetrachlorophenyl; the moiety in formula (II)

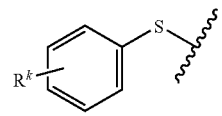

is preferably connected in the meta or para position relative to the sulfonium substituent;

$R^g$, $R^h$, $R^i$ and $R^k$ are independently of one another H, —$OCH_3$, —$OCH_2CH_3$, methyl, ethyl, i-propyl, —$CH_2CH_2OH$, —$CH_2CH_2SH$, preferably the substituents $R^g$, $R^h$, $R^i$ and $R^k$ are in a para position to at least one of the sulfur atoms, more preferably $R^g$, $R^h$, $R^i$ and $R^k$ are H. Preferably $R^x$ is aryl and n is an integer from 1 to 5.

Preferably the cationic photoinitiator (A) may be represented by the following formula (III)

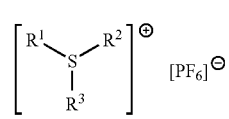

(III)

wherein $R^1$, $R^2$ and $R^3$ are each independently of one another $C_{6-18}$ aryl or heteroaryl that is unsubstituted or substituted.

$C_{6-18}$ aryl are preferably selected from phenyl, naphthyl, anthryl or phenanthryl. Examples of substituted $C_{6-18}$ aryl are phenyl, naphthyl, anthryl or phenanthryl which are substituted with one or more radicals selected from the group consisting of substituted or unsubstituted alkyl, preferably $C_{1-12}$-alkyl, alkoxy, preferably $C_{1-6}$-alkoxy, alkylthio, preferably $C_{1-6}$-alkylthio, halogen or arylthio and mixture thereof more preferably the radicals are selected from the group comprising methyl, ethyl, n-propyl, isopropyl, n-butyl, sec-butyl, isobutyl, tert-butyl, the various pentyl or hexyl isomers, hydroxymethyl, hydroxyethyl, sulfanylmethyl, sulfanylethyl, methoxy, ethoxy, propoxy, butoxy, pentyloxy, hexyloxy, methylthio, ethylthio, propylthio, butylthio, pentylthio, hexylthio, fluorine, chlorine, bromine, iodine or phenylthio and mixture thereof.

Preferred cationic photoinitiator(s) (A) are sulfonium hexafluorophosphate salts according to formula (IV)

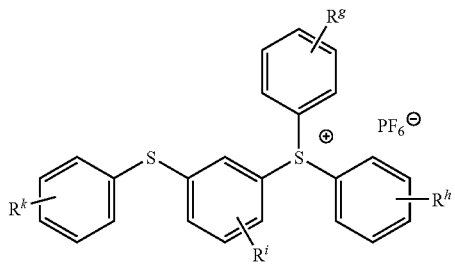
(IV)

wherein $R^g$, $R^h$, $R^i$ and $R^k$ are independently of one another H, —OCH$_2$CH$_3$, methyl, ethyl, i-propyl, —CH$_2$CH$_2$OH, —CH$_2$CH$_2$SH, preferably the substituents $R^g$, $R^h$, $R^i$ and $R^k$ are in a para position to at least one of the sulfur atoms, more preferably $R^g$, $R^h$, $R^i$ and $R^k$ are H.

Furthermore, the cationic photoinitiator (A) can also be selected from the group comprising sulfonium salts which have at least two sulfonium groups in one molecule and the respective fluorophosphate anions as defined in formula (I).

An example of a photoinitiator (A) with two sulfonium groups is presented in the following formula (V)

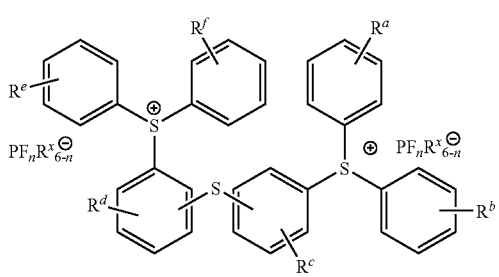
(V)

wherein n is an integer from 1 to 6, preferably an integer from 4 to 6, most preferably n is 6, i.e. hexafluorophosphate (PF$_6^\ominus$); $R^x$ is substituted or unsubstituted $C_{1-6}$-alkyl; or substituted or unsubstituted aryl or heteroaryl, preferably $R^x$ is unsubstituted $C_{1-6}$-alkyl selected from methyl, ethyl, propyl, isopropyl; or unsubstituted aryl selected from phenyl or naphthyl; or substituted aryl selected from halogenated aryl preferably fluorinated and/or chlorinated aryl groups, in particular pentafluorophenyl, pentachlorophenyl, tetrafluorophenyl or tetrachlorophenyl; the moiety

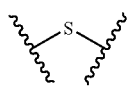

in formula (V) is preferably connecting the sulfonium moieties such that the sulphur is in the para position relative to both sulfonium substituents or such that the sulphur is in the ortho relative to one sulfonium substituent and in the meta position relative to the other sulfonium substituent;
$R^a$, $R^b$, $R^c$, $R^d$, $R^e$ and $R^f$ are independently of one another H, —OCH$_3$, —OCH$_2$CH$_3$, methyl, ethyl, i-propyl, —CH$_2$CH$_2$OH, —CH$_2$CH$_2$SH, preferably the substituents $R^a$, $R^b$, $R^c$, $R^d$, $R^e$ and $R^f$, are in a para position to at least one of the sulfur atoms, more preferably $R^a$, $R^b$, $R^c$, $R^d$, $R^e$ and $R^f$ are H. Preferably $R^x$ is aryl and n is an integer from 1 to 5.

An example of a photoinitiator (A) which presents two sulfonium groups and which is of particular interest is presented by the following formula (VI):

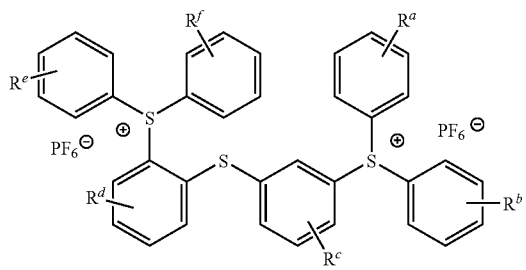
(VI)

wherein $R^a$, $R^b$, $R^c$, $R^d$, $R^e$ and $R^f$ are independently of one another H, —OCH$_3$, —OCH$_2$CH$_3$, methyl, ethyl, i-propyl, —CH$_2$CH$_2$OH, —CH$_2$CH$_2$SH, preferably the substituents $R^a$, $R^b$, $R^c$, $R^d$, $R^e$ and $R^f$, are in a para position to at least one of the sulfur atoms, more preferably $R^a$, $R^b$, $R^c$, $R^d$, $R^e$ and $R^f$ are H.

Further preferred is the cationic photoinitiator (A) which is represented by a mixture comprising

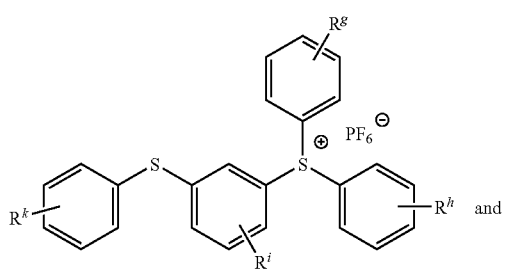
(IV)

and

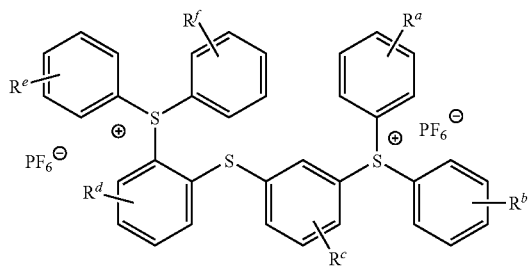
(VI)

wherein $R^a$, $R^b$, $R^c$, $R^d$, $R^e$, $R^f$, $R^g$, $R^h$, $R^i$ and $R^k$ are independently of one another H, —OCH$_3$, —OCH$_2$CH$_3$, methyl, ethyl, i-propyl, —CH$_2$CH$_2$OH, —CH$_2$CH$_2$SH, preferably the substituents $R^b$, $R^c$, $R^d$, $R^e$, $R^f$, $R^g$, $R^h$, $R^i$ and $R^k$ are in a para position to at least one of the sulfur atoms, more preferably $R^a$, $R^b$, $R^c$, $R^d$, $R^e$, $R^f$, $R^g$, $R^h$, $R^i$ and $R^k$ are H.

In particular improved results have been obtained with a cationic photoinitiator (A) comprising a mixture of the above mentioned sulfonium hexafluorophosphate salts according to formula (IV) and (VI) wherein the weight ratio of (IV) to (VI) is between 5:1 to 1:5, preferably 5:2 to 2:5, more preferably 5:4 to 4:5 in particular about 1:1.

Commercially available triarylsulfonium hexafluorophosphate salts (mix of mono and bis salts): Cyracure UVI6992 from Dow Chemicals, CPI 6992 from Aceto Carp, Esacure 1064 from Lamberti, Omnicat 432 from IGM; Triarylsulfonium hexafluorophosphate salt (bis salt only): SP-55 from Asahi-Denka; Modified sulfonium hexafluorophosphate salt: Esacure 1187 from Lamberti; Bis[4-di(4-(2-hydroxyethyl) phenyl)sulphonio]-phenyl]sulphide bis-hexafluorophosphate: SP-150 from Asahi-Denka.

Cationic Photoinitiator (B)

The second essential cationic photoinitiator (B) is different from photoinitiator (A) i.e. photoinitiator (B) is not a sulfonium salt with a fluorophosphate anion as defined in formula (I).

Examples of the cationic photoinitiator (B) are onium salts having a structure shown by the following formula (VII). The onium salt liberates a Lewis acid upon exposure to light.

According to a preferred embodiment of the present invention the cationic photoinitiator (B) is selected from at least one onium salt having a structure according to the following formula (VII)

i. $[R^1_a R^2_b R^3_c R^4_d E]^+ [MX_{n+1}]^-$ (VII)

wherein
E represents S, P, O, I or N≡N;
$R^1$, $R^2$, $R^3$ and $R^4$ represent individually the same or different organic group selected from substituted or unsubstituted $C_{6-18}$ aryl;
a, b, c, and d independently represent an integer from 0 to 3, and provided that a+b+c+d is 3 if E=S, 4 if E=P, 3 if E=O, 2 if E=I and 1 if E=N≡N;
M represents a metal or metalloid selected from the group consisting of B, P, As, Sb, Fe, Sn, Bi, Al;
X represents F, Cl, Br, a substituted or unsubstituted aryl or heteroaryl group or mixtures thereof and;
n is the valence number of M
with the proviso that the onium salt is not a sulfonium salt wherein the anion is a fluorophosphate defined by the following formula (I):

$PF_n R^x_{6-n}{}^\ominus$ (I)

with n=1 to 6 and
$R^x$=substituted or unsubstituted $C_{1-6}$-alkyl or substituted or unsubstituted aryl or heteroaryl.

Preferably in the above mentioned formula (VII) $R^1$, $R^2$, $R^3$ and $R^4$ represent individually the same or different organic group selected from phenyl, naphthyl, anthryl or phenanthryl, or substituted $C_{6-18}$ aryl which are substituted with one or more radicals selected from the group consisting of substituted or unsubstituted alkyl, preferably $C_{1-12}$-alkyl, alkoxy, preferably $C_{1-6}$-alkoxy, alkylthio, preferably $C_{1-6}$-alkylthio, halogen or arylthio and mixture thereof more preferably the radicals are selected from the group consisting of methyl, ethyl, n-propyl, isopropyl, n-butyl, sec-butyl, iso-butyl, tent-butyl, the various pentyl or hexyl isomers, hydroxymethyl, hydroxyethyl, sulfanylmethyl, sulfanylethyl, methoxy, ethoxy, prop oxy, butoxy, pentyloxy, hexyloxy, methylthio, ethylthio, propylthio, butylthio, pentylthio, hexylthio, fluorine, chlorine, bromine, iodine or phenylthio and mixture thereof.

In particular $R^1$, $R^2$, $R^3$ and $R^4$ of the above mentioned formula (VII) represent individually the same or different organic group selected from phenyl, tolyl, cumyl, methoxyphenyl, hydroxyethylphenyl, sulfanylethylphenyl, hydroxyalkyloxyphenyl, diphenylthioether or $C_{1-12}$-alkylphenyl and mixtures thereof.

X represents F, Cl, Br, a substituted or unsubstituted aryl or heteroaryl group or mixtures thereof.

Examples of X are halogenated aryl groups, preferably fluorinated and/or chlorinated aryl groups, in particular pentafluorophenyl, pentachlorophenyl, tetrafluorophenyl or tetrachlorophenyl.

Preferably the cationic photoinitiator (B) may be selected from the group consisting of iodonium salts and/or hexafluoroantimonate salts.

The cationic photoinitiator (B) may be represented by the following formula (VIII)

$$\left[ \begin{array}{c} R^1 \diagdown \diagup R^2 \\ S \\ | \\ R^3 \end{array} \right]^\oplus \quad [SbF_6]^\ominus$$ (VIII)

wherein $R^1$, $R^2$ and $R^3$ are each independently of one another $C_{6-18}$ aryl or heteroaryl that is unsubstituted or substituted.

$C_{6-18}$ aryl are preferably selected from phenyl, naphthyl, anthryl or phenanthryl. Examples of substituted $C_{6-18}$ aryl are phenyl, naphthyl, anthryl or phenanthryl which are substituted with one or more radicals selected from the group consisting of substituted or unsubstituted alkyl, preferably $C_{1-12}$-alkyl, alkoxy, preferably $C_{1-6}$-alkoxy, alkylthio, preferably $C_{1-6}$-alkylthio, halogen or arylthio and mixture thereof, more preferably the radicals are selected from the group consisting of methyl, ethyl, n-propyl, isopropyl, n-butyl, sec-butyl, iso-butyl, tert-butyl, the various pentyl or hexyl isomers, hydroxymethyl, hydroxyethyl, sulfanylmethyl, sulfanylethyl, methoxy, ethoxy, propoxy, butoxy, pentyloxy, hexyloxy, methylthio, ethylthio, propylthio, butylthio, pentylthio, hexylthio, fluorine, chlorine, bromine, iodine or phenylthio and mixture thereof.

The cationic photoinitiator (B) is preferably presented by a sulfonium hexafluoroantimonate salt according to the following formula (IX)

wherein $R^g$, $R^h$, $R^i$ and $R^k$ have the same meaning as in formula (IV).

Furthermore, the cationic photoinitiator (B) can also be selected from the group comprising sulfonium hexafluoroantimonate salts which have at least two sulfonium groups in one molecule and the hexafluoroantimonate anions. An example of a photoinitiator (B) which have two sulfonium groups and which is of particular interest is presented by formula (X):

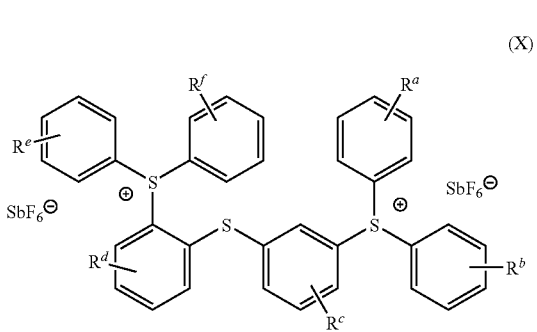

wherein $R^a$, $R^b$, $R^c$, $R^d$, $R^e$ and $R^f$ have the same meaning as in formula (VI).

The cationic photoinitiator (B) is preferably represented by a mixture comprising (a)

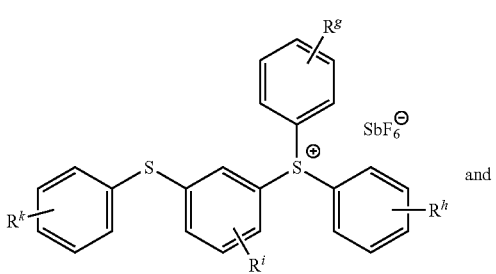

and (b)

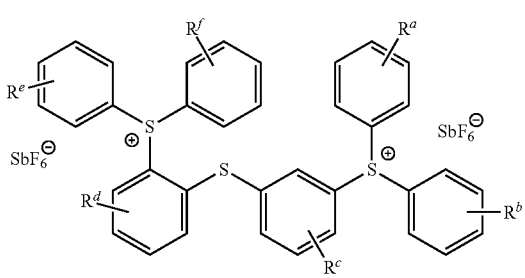

wherein $R^a$, $R^b$, $R^c$, $R^d$, $R^e$, $R^f$, $R^g$, $R^h$, $R^i$ and $R^k$ have the same meaning as in formulas (IV) and (VI)

In particular improved results have been obtained with a cationic photoinitiator (B) comprising a mixture of the above mentioned sulfonium hexafluoroantimonate salts according to formula (IX) and (X) wherein the weight ratio of (IX) to (X) is between 5:1 to 1:5, preferably 5:2 to 2:5, more preferably 5:4 to 4:5 in particular about 1:1.

Furthermore the cationic photoinitiator (B) can be selected from iodonium salts.

Preferably the cationic photoinitiator (B) comprises at least one iodonium salt selected from the group consisting of (tolylcumyl)iodonium tetrakis(pentafluorophenyl)borate, (4-methylphenyl)(4-(2-methylpropyl)phenyl)iodonium hexafluorophosphate, bis(4-methylphenyl)iodonium hexafluorophosphate, bis(dodecylphenyl)iodonium hexafluorophosphate, bis(4-hexylphenyl)iodonium hexafluoroantimonate; bis(4-hexylphenyl)iodonium hexafluorophosphate; (4-hexylphenyl)phenyliodonium hexafluoroantimonate; (4-hexylphenyl)phenyliodonium hexafluorophosphate; bis(4-octylphenyl)iodonium hexafluoroantimonate; (4-sec-butylphenyl)-(4-methylphenyl)iodonium hexafluorophosphate; (4-iso-propylphenyl)-(4-methylphenyl)iodonium hexafluorophosphate; [4-(2-hydroxytetradecyl-oxy)phenyl]phenyliodonium hexafluoroantimonate; [4-(2-hydroxydodecyloxy)phenyl] phenyliodonium hexafluoroantimonate; bis(4-octylphenyl) iodonium hexafluorophosphate; (4-octylphenyl)phenyliodonium hexafluoroantimonate; (4-octylphenyl) phenyliodonium hexafluorophosphate; bis(4-decylphenyl) iodonium hexafluoroantimonate; bis(4-decylphenyl) iodonium hexafluorophosphate; (4-decylphenyl) phenyliodonium hexafluoroantimonate; (4-decylphenyl) phenyliodonium hexafluorophosphate; (4-octyloxyphenyl) phenyliodonium hexafluoroantimonate; (4-octyloxyphenyl) phenyliodonium hexafluorophosphate; (2-hydroxydodecyloxyphenyl)phenyliodonium hexafluoroantimonate; (2-hydroxydodecyloxyphenyl)phenyliodonium hexafluorophosphate; bis(4-hexylphenyl)iodonium tetrafluoroborate; (4-hexylphenyl)phenyliodonium tetrafluoroborate; bis(4-decylphenyl) tetrafluoroborate; (4-octylphenyl)phenyliodonium tetrafluoroborate; bis(4-decylphenyl) iodonium tetrafluoroborate; bis(4-(mixed $C_4$-$C_8$-alkyl) phenyl)iodonium hexafluoroantimonate; (4-decylphenyl) phenyliodonium tetrafluoroborate; (4-octyloxyphenyl)-phenyliodonium tetrafluoroborate; (2-hydroxydodecyloxyphenyl)phenyliodonium tetrafluoroborate; biphenylene iodonium tetrafluoroborate; biphenyleneiodonium hexafluorophosphate; and biphenyleneiodonium hexafluoroantimonate.

In a preferred embodiment the cationic photoinitiator (B) is an iodonium tetrakis(pentafluorophenyl)borate, preferably (tolylcumyl)iodonium tetrakis(pentafluorophenyl)borate.

Examples of cationic photoinitiator (B) which are commercially available and which are of particular interest are triarylsulfonium hexafluoroantimonate salts (mix of mono and bis salts): Cyracure UVI6976 from Dow Chemicals, CPI 6976 from Aceto Corp, Ki78 from Adeka; Bis-[4-di(4-(2-hydroxyethyl)phenyl)sulphonio]-phenyl]sulphide bis-hexafluoroantimonate: SP-170 from Asahi-Denka; Iodonium salts: bis(dodecylphenyl)iodonium hexafluorophosphate: UV1242 from Deuteron;

bis(4-methylphenyl)iodonium hexafluorophosphate: UV2257 from Deuteron, Omnicat 440 from IGM; (4-methylphenyl)(4-(2-methylpropyl)phenyl)iodonium hexafluorophosphate: Irgacure 250 from Ciba SC; (tolylcumyl)iodonium tetrakis (pentafluorophenyl)borate: rhodorsil 2074 from Rhodia; Thioxantene salts: 10-biphenyl-4-yl-2-isopropyl-9-oxo-9H-thioxanthene-10ium hexafluorophosphate: Omnicat 550 from IGM; adduct of 10-biphenyl-4-yl-2-isopropyl-9-oxo-9H-thioxanthene-10ium hexafluorophosphate with a polyol: Omnicat 650 from IGM; Metallocene salts: cumenyl cyclopentadienyl iron (II) hexafluorophosphate: Irgacure 261 from Ciba SC; Naphthalenylcyclopentadienyl iron (II) hexafluorophosphate, benzyl cyclopentadienyl iron (II) hexafluorophosphate, Cyclopentadienyl carbazole iron (II) hexafluorophosphate.

According to a preferred embodiment of the present invention the cationic photoinitiator composition comprises a cationic photoinitiator (A) which is represented by the following formula (III)

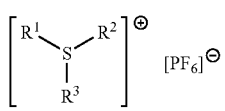

and a cationic photoinitiator (B) which is represented by the following formula (VIII)

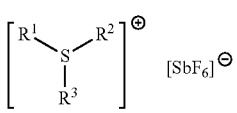

wherein independent of formula (III) or formula (VIII) $R^1$, $R^2$ and $R^3$ are each independently of one another $C_{6-18}$ aryl or heteroaryl that is unsubstituted or substituted. In particular $R^1$, $R^2$ and $R^3$ have the same meaning as in the formulas (III) and (VIII) defined above.

The photoinitiator composition according to the present invention is preferably used either in cationically polymerisable compositions, or in hybrid compositions containing both cationically and free radically-polymerising species.

Other Optional Compounds

The photoinitiator composition may further comprise at least one free-radical photoinitiator and/or photosensitizer.

The free radical photoinitiator may be chosen from those commonly used to initiate radical photopolymerization. Examples of free radical photoinitiators include benzoins, e.g., benzoin, benzoin ethers such as benzoin methyl ether, benzoin ethyl ether, benzoin isopropyl ether, benzoin phenyl ether, and benzoin acetate; acetophenones, e.g., acetophenone, 2,2-dimethoxyacetophenone, and 1,1-dichloroacetophenone; benzyl ketals, e.g., benzyl dimethylketal and benzyl diethyl ketal; anthraquinones, e.g., 2-methylanthraquinone, 2-ethylailthraquinone, 2-tertbutylanthraquinone, 1-chloroanthraquinone and 2-amylanthraquinone; triphenylphosphine; benzoylphosphine oxides, e.g., 2,4,6-trimethylbenzoy-diphenylphosphine oxide (Luzirin TPO); bisacylphosphine oxides; benzophenones, e.g., benzophenone and 4,4'-bis(N,N-dimethylamino)benzophenone; thioxanthones and xanthones; acridine derivatives; phenazine derivatives; quinoxaline derivatives; 1-phenyl-1,2-propanedione 2-O-benzoyl oxime; 4-(2-hydroxyethoxy)phenyl-(2-propyl)ketone (Irgacure® 2959); 1-aminophenyl ketones or 1-hydroxy phenyl ketones, e.g., 1-hydroxycyclohexyl phenyl ketone, 2-hydroxyisopropyl phenyl ketone, phenyl-1-hydroxyisopropyl ketone, and 4-isopropylphenyl 1-hydroxyisopropyl ketone. Polymeric free radical photoinitiators may also be used, such as Genopol BP-1 from Rahn.

Preferably, the free radical photoinitiator is a cyclohexyl phenyl ketone. More preferably, the cyclohexyl phenyl ketone is a 1-hydroxycyclohexyl phenyl ketone, e.g., Irgacure® 184. The free radical photoinitiator may comprise one free radical photoinitiator or two or more free radical photoinitiators.

The at least one free-radical photoinitiator may be present in the photoinitiator composition in an amount of 0.1 to 90 wt.-%, preferably in an amount of 5 to 80 wt.-%, more preferably from 15 to 70 wt.-%, especially from 20 to 60 wt.-%, and more especially 25 to 50 wt.-% based on the total amount of the photoinitiator composition.

Sensitisers

A sensitiser is usually not mandatory for initiation to occur. It will, however, greatly enhance the performance of the initiator under certain conditions. It may also be added to shift the absorption characteristics of a system. These are normally towards longer wavelengths and this is referred to as a redshift.

Examples of sensitizers are anthracene, perylene, phenothiazine, xanthone, thioxanthone, benzophenone, ethyl-4-dimethylaminobenzoate (esacure EDB).

Further photosensitizer include thioxantone derivatives: e.g.: 2,4-diethylthioxanthone (DETX), 1-chloro-4-propoxythioxanthone (CPTX) and isopropyl thioxanthone (ITX) from the Lambson Ltd SPEEDCURE range, and anthracene derivatives: e.g.: 2-ethyl-9,10-dimethoxyanthracene (EDMA), 9-hydroxy-methyl-anthracene (HMA) from Sigma-Aldrich and 9,10-dibutoxyanthracene for the Kawasaki Kasei Chemicals LTS Anthracure range.

Other sensitizers are sterically hindered amines and especially amino benzoate sensitizers such as BEDB, DMB, EDB and EHA available from Lambson Chemicals Ltd and esacure EDB and EHA from Sartomer.

Preferably the photosensitizer is present in the photoinitiator composition in an amount of 0.1 to 90 wt.-%, preferably in an amount of 5 to 80 wt.-%, more preferably from 15 to 70 wt.-% and especially from 35 to 60 wt.-% based on the total amount of the photoinitiator composition.

Additionally, the photoinitiator composition according to the present invention may comprise one or more electron donor components. The electron donor component is preferably present in the photoinitiator composition in an amount of 0.1 to 90 wt.-%, further preferred in an amount of 5 to 80 wt.-%, more preferably from 15 to 70 wt.-% and especially from 35 to 60 wt.-% based on the total amount of the composition.

The person skilled in the art can use Photo DSC to determine suitable electron donor components which provide the best stability for the selected photoinitiator composition or for the selected photocurable composition.

Photocurable Composition

A further embodiment of the present invention is a photocurable composition.

The photocurable composition comprises at least a photoinitiator composition according to the present invention.

Preferably, the photocurable composition comprises the photoinitiator composition as described herein in an amount between 0.1 to 30% by weight, preferably between 0.5 and 20% by weight, more preferably between 1 and 10% by weight, wherein the percent by weight is based on the total weight of the photocurable composition.

The photocurable composition preferably comprises a canonically curable component.

Canonically Curable Component

Preferably, the cationically curable component is selected from the group consisting of cationically-polymerisable components reacting via a ring opening mechanism preferably selected from the group comprising epoxy compounds, oxetanes, tetrahydropyranes, lactones and mixtures thereof.

The cationically curable compound may also be a cyclic ether compound, acetal compound, cyclic thioether compound, Spiro orthoester compound or vinylether compound.

Preferably, the cationically curable component is present in an amount of 2 to 90% by weight, more preferred in an amount of 10 to 85% by weight, more preferably 20 to 80% by weight, wherein the percent by weight is based on the total weight of the photocurable composition.

Preferred examples of commercial epoxy-containing compounds suitable for use in the present invention are selected from the group consisting of Uvacure® 1500 (3,4-epoxycyclohexylmethyl-3',4'-epoxycyclohexanecarboxylate, available from UCB Chemicals Corp.); Epalloy® 5000 (epoxidized hydrogenated Bisphenol A, available from CVC Specialties Chemicals, Inc.); Heloxy® 48 (trimethylol propane triglycidyl ether, available from Resolution Performance Products LLC); Heloxy® 107 (diglycidyl ether of cyclohexanedimethanol, available from Resolution Performance Products LLC); Uvacure® 1501 and 1502 which are proprietary cycloaliphatic epoxides, Uvacure® 1530-1534 which are cycloaliphatic epoxides blended with a proprietary polyol, Uvacure® 1561 and Uvacure® 1562 which are proprietary cycloaliphatic epoxides having a (meth)acrylic unsaturation (all available from UCB Chemicals Corp.); Cyracure® UVR-6100, -6105, -6107, and -6110 which are all 3,4-epoxycyclohexylmethyl-3',4'-epoxycyclohexanecarboxylate, Cyracure® UVR-6128, a bis(3,4-epoxycyclohexyl)adipate (all available from Dow Chemical Co.); Araldite® CY 179, a 3,4-epoxycyclohexylmethyl-3',4'-epoxycyclohexanecarboxylate and Araldite® PY 284, a digycidyl hexahydrophthalate polymer (available from Huntsman Advanced Materials Americas Inc.); Celloxide® 2021, Celloxide® 2021 P, 3,-4-epoxycyclohexylmethyl 3',-4'-epoxycyclohexane-carboxylate, Celloxide® 2081, a 3,-4-epoxycyclohexylmethyl 3',-4'-epoxycyclohexane-carboxylate modified caprolactone, Celloxide® 2083, Celloxide® 2085, Celloxide® 2000, Celloxide® 3000, Epolead® GT-300, Epolead® GT-302, Epolead® GT-400, Epolead® 401, Epolead® 403 (all available from Daicel Chemical Industries Co., Ltd.); DCA, an alicyclic epoxy (available from Asahi Denka Co. Ltd); and E1, an epoxy hyperbranched polymer obtained by the polycondensation of 2,2-dimethylolpropionic acid functionalized with glycidyl groups (available from Perstoip AB). The epoxy compounds can also be a siloxane based epoxy such as 1,3-bis(3-(2,3-epoxypropoxy)propyl) tetramethyldisiloxane and/or epoxidized cyclic silanes such as 2,4,6,8,10-pentakis(3-(2,3-epoxypropoxy)propyl)-2,4,6,8,10-pentamethylcyclopentasiloxane.

Further epoxy-containing compounds such as Erisys GE 30, Erisys GE 36 from CVC Chemicals can be used.

Furthermore, all the epoxidized siloxanes described in the U.S. Pat. No. 5,639,413 are suitable for use in the present invention.

Preferably the canonically curable compound has a cycloaliphatic or a perhydrogenated backbone. Particularly preferred are epoxy-containing compounds selected from the group consisting of 3,4-epoxycyclohexylmethyl-3',4'-epoxycyclohexanecarboxylate and hydrogenated bisphenol A diglycidyl ether.

The oxetane compound may contain one or more oxetane groups. Preferably, the compound has less than 20, and in particular less than 10 oxetane groups. In particularly preferred embodiments the oxetane compound has two oxetane groups. It may also be useful to use mixtures of oxetane compounds, in particular those having 1, 2, 3, 4 or 5 oxetane groups. The oxetane compound preferably has a molecular weight of about 100 or more, preferably of about 200 or more. Generally, this compound will have a molecular weight of about 10,000 or lower, preferably of about 5,000 or lower.

The oxetane groups preferably are radiation curable oligomers having a phenyl, (oligo)-bis-phenyl, polysiloxane or polyether backbone. Examples of polyethers are e.g. poly-THF, polypropylene glycol, alkoxylated trimethylolpropane, alkoxylated pentaerytritol and the like.

Preferably, the oxetane compound has one or more groups according to formula (1)

a.

wherein $R^1$ is a group of the formula (2)

i. $CH_2-X-R^3$ (2)

wherein X is O or S and
$R^2$ and $R^3$ are the remainder of the molecule.

Examples of the compound having one oxetane ring are compounds according to formula (1), wherein X represents an oxygen atom or a sulfur atom, $R^2$ represents a hydrogen atom; fluorine atom; alkyl group having from 1 to 6 carbon atoms such as a methyl group, ethyl group, propyl group, butyl group and the like; fluoroalkyl group having from 1 to 6 carbon atoms such as a trifluoromethyl group, perfluoroethyl group, perfluoropropyl group, and the like; aryl group having from 6 to 18 carbon atoms such as a phenyl group, naphthyl group, or the like; furyl group; or thienyl group, and $R^3$ represents a hydrogen atom, alkyl group having from 1 to 6 carbon atoms such as a methyl group, ethyl group, propyl group, butyl group, and the like; alkenyl group having from 2 to 6 carbon atoms such as an 1-propenyl group, 2-propenyl group, 2-methyl-1-propenyl group, 2-methyl-2-propenyl group, 1-butenyl group, 2-butenyl group, 3-butenyl group, and the like; aryl group having from 6 to 18 carbon atoms such as a phenyl group, naphthyl group, anthonyl group, phenanthryl group, and the like; aralkyl group having from 7 to 18 carbon atoms which may be either substituted or unsubstituted, such as a benzyl group, fluorobenzyl group, methoxybenzyl group, phenethyl group, styryl group, cinnamyl group, ethoxybenzyl group, and the like; group having other aromatic groups such as an aryloxyalkyl group including a phenoxymethyl group, phenoxyethyl group or the like; alkylcarbonyl group having from 2 to 6 carbon atoms such as an ethylcarbonyl group, propylcarbonyl group, butylcarbonyl group, and the like; alkoxycarbonyl group having from 2 to 6 carbon atoms such as an ethoxycarbonyl group, propoxycarbonyl group, butoxycarbonyl group, and the like; or N-alkylcarbamoyl group having from 2 to 6 carbon atoms such as an ethylcarbamoyl group, propylcarbamoyl group, butylcarbamoyl group, pentylcarbamoyl group, and the like.

The oxetane compounds having two oxetane rings, include for example those compounds represented by the following formula (3)

a.

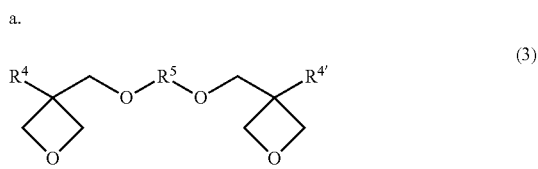

Wherein $R^4$ and $R^{4'}$ independently represent a group of the above formula (2), $R^5$ is a linear or branched alkylene group having from 1 to 20 carbon atoms such as an ethylene group, propylene group, butylene group, and the like; linear or branched poly(alkylenoxy) group having from 1 to 120 carbon atoms such as poly(ethylenoxy) group, poly(propylenoxy) group, and the like; linear or branched unsaturated hydrocarbon group such as a propenylene group, methylpropenylene group, butenylene group, and the like; carbonyl group, alkylene group containing a carbonyl group, alkylene group containing a carboxyl group in the middle of a molecular chain, and alkylene group containing a carbamoyl group in the middle of a molecular chain. Also in the compounds of formula (3), $R^5$ may be a polyvalent group represented by any one of the following formulas (4) to (6):

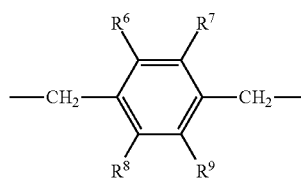

(4)

wherein $R^6$, $R^7$, $R^8$ and $R^9$ represent independently from each other a hydrogen atom; an alkyl group having from 1 to 4 carbon atoms such as a methyl group, an ethyl group, a propyl group, a butyl group, and the like; alkoxy group having from 1 to 4 carbon atoms such as a methoxy group, an ethoxy group, a propyoxy group, a butoxy group, and the like; halogen atom such as a chlorine atom, a bromine atom, and the like; a nitro group, a cyano group, a mercapto group, a lower alkylcarboxyl group, a carboxyl group, or a carbamoyl group,

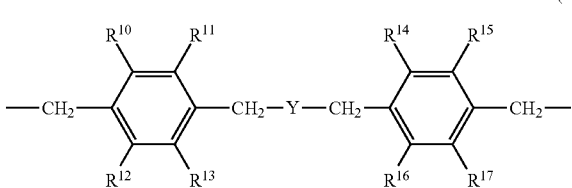

(5)

wherein Y represents an oxygen atom, a sulfur atom, a methylene group, and groups represented by the formulae —NH—, —SO—, —SO$_2$—, —C(CF$_3$)$_2$—, or —C(CH$_3$)$_2$—, and $R^{10}$ to $R^{17}$ independently may have the same meaning as $R^6$ to $R^9$ as defined above,

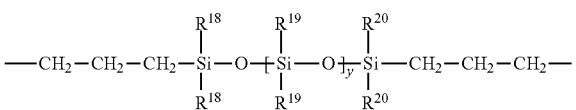

(6)

wherein $R^{18}$ and $R^{20}$ independently represent an alkyl group having from 1 to 4 carbon atoms such as a methyl group, an ethyl group, a propyl group, a butyl group, or the like, or an aryl group having from 6 to 18 carbon atoms such as a phenyl group, a naphthyl group, and the like, y denotes an integer of from 0 to 200, and $R^{19}$ represents an alkyl group having from 1 to 4 carbon atoms such as a methyl group, an ethyl group, a propyl group, a butyl group, and the like or an aryl group having from 6 to 18 carbon atoms such as a phenyl group, a naphthyl group, and the like. Alternatively, $R^{19}$ may be a group represented by the following formula (7)

2.

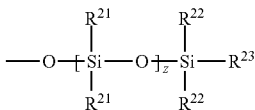

(7)

wherein $R^{21}$, $R^{22}$ and $R^{23}$ independently represent an alkyl group having from 1 to 4 carbon atoms such as a methyl group, an ethyl group, a propyl group, a butyl group, or the like, or an aryl group having from 6 to 18 carbon atoms such as a phenyl group, a naphthyl group, or the like, and z is an integer of from 0 to 100.

Examples of preferred compounds containing one oxetane ring in its molecule are 3-ethyl-3-hydroxymethyloxetane, 3-(meth)allyloxymethyl-3-ethyloxetane, (3-ethyl-3-oxetanyl-methoxy)methylbenzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3 oxetanylmethoxy)-ethyl]phenyl ether, isobutoxymethyl(3-ethyl-3-oxetanylmethyl)ether, isobomyloxyethyl(3-ethyl-3-oxetanylmethyl)ether, isobornyl(3-ethyl-3 oxetanylmethyl) ether, 2-ethylhexyl(3-ethyl-3-oxetanylmethyl)ether, ethyldiethylene glycol(3 ethyl-3-oxetanylmethyl)ether, dicyclopentadiene(3-ethyl-3-oxetanylmethyl)ether, dicyclopentenyloxyethyl(3-ethyl-3-oxetanylmethyl)ether, dicyclopentenyl(3-ethyl-3-oxetanylmethyl)ether, tetrahydrofurfuryl(3-ethyl-3-oxetanylmethyl)ether, tetrabromophenyl(3-ethyl-3-oxetanylmethyl)ether, 2-tetrabromophenoxyethyl(3-ethyl-3-oxetanylmethyl)ether, tribromophenyl(3-ethyl-3-oxetanylmethyl)ether, 2-tribromophenoxyethyl(3 ethyl-3-oxetanylmethyl)ether, 2-hydroxyethyl(3-ethyl-3-oxetanylmethyl)ether, 2-hydroxypropyl(3-ethyl-3-oxetanylmethyl)ether, butoxyethyl(3-ethyl-3 oxetanylmethyl)ether, pentachlorophenyl(3-ethyl-3-oxetanylmethyl)ether, pentabromophenyl(3-ethyl-3-oxetanylmethyl)ether, bornyl(3-ethyl-3-oxetanylmethyl)ether, and the like. Other examples of oxetane compounds suitable for use include trimethylene oxide, 3,3-dimethyloxetane, 3,3-dichloromethyloxetane, 3,3-[1,4-phenylene-bis(methyleneoxymethylene)]-bis(3-ethyloxetane), 3-ethyl-3-hydroxymethyloxetane, and bis-[(1-ethyl(3-oxetanyl)methyl)]ether.

Examples of compounds having two or more oxetane rings in the compound which may be used in the present invention include: 3,7-bis(3-oxetanyl)-5-oxa-nonane, 3,3'-(1,3-(2-methylenyl)propanediylbis(oxymethylene))bis-(3-ethyloxetane), 1,4-bis[(3-ethyl-3-oxetanylmethoxy)methyl]benzene, 1,2-bis[(3 ethyl-3-oxetanylmethoxy)methyl]ethane, 1,3-bis[(3-ethyl-3-oxetanylmethoxy)methy]propane, ethylene glycol bis(3-ethyl-3 oxetanyl methyl)ether, dicyclopentenyl bis(3-ethyl-3 oxetanylmethyl)ether, triethylene glycol bis(3-ethyl-3-oxetanylmethyl)ether, tetraethylene glycol bis(3-ethyl-3-oxetanylmethyl)ether, tricyclodecanediyldimethylene(3-ethyl-3-oxetanylmethyl) ether, trimethylolpropane tris(3-ethyl-3-oxetanylmethyl) ether, 1,4-bis(3-ethyl-3-oxetanylmethoxy)butane, 1,6-bis(3-ethyl-3-oxetanylmethoxy)hexane, pentaerythritol tris(3-ethyl-3-oxetanylmethyl)ether, pentaerythritol tetrakis(3-ethyl-3-oxetanylmethyl)ether, polyethylene glycol bis(3 ethyl-3-oxetanylmethyl)ether, dipentaerythritol hexakis(3 ethyl-3-oxetanylmethyl)ether, dipentaerythritol pentakis(3-ethyl-3-oxetanylmethyl)ether, dipentaerythritol tetrakis(3-ethyl-3-oxetanylmethyl)ether, caprolactone-modified dipentaerythritol hexakis(3-ethyl-3-oxetanylmethyl)ether, caprolactone-modified dip entaerythritol pentakis(3-ethyl-3 oxetanylmethyl)ether, ditrimethylolpropane tetrakis(3-ethyl-3-oxetanylmethyl)ether, EO-modified Bisphenol A bis(3-ethyl-3-oxetanylmethyl)ether, PO-modified Bisphenol A bis(3-ethyl-3-oxetanylmethyl)ether, EO-modified hydrogenated Bisphenol A bis(3-ethyl-3-oxetanylmethyl)ether, PO-modified hydrogenated Bisphenol A bis(3-ethyl-3-oxetanylmethyl)ether, EO-modified Bisphenol F (3-ethyl-3-oxetanylmethyl)ether, and the like.

Of the above compounds, it is preferable that the oxetane compounds have 1-10, preferably 1-4, and even more preferably 1 oxetane rings in the compound. Specifically, 3-ethyl-3-hydroxymethyl oxetane, (3-ethyl-3-oxetanylmethoxy)methylbenzene, 1,4-bis[(3-ethyl-3-oxetanylmethoxy)methyl]benzene, 1,2-bis(3-ethyl-3-oxetanylmethoxy)ethane and trimethylolpropane tris(3-ethyl-3-oxetanylmethyl)ether are preferably used. Commercially available oxetane compounds include Cyracure® UVR 6000 (available from Dow Chemical Co.) and Aron Oxetane OXT-101, OXT-121, OXT-211, OXT-212, OXT-221, OXT-610 and OX-SQ (available from Toagosei Co. Ltd.).

In a further preferred embodiment, the following oxetane compounds can be used in present invention:

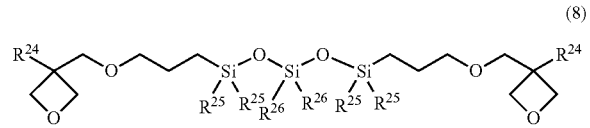

(8)

wherein $R^{24}$ represents a hydrogen atom, a fluorine atom, an alkyl group having 1-6 carbon atoms such as a methyl group, an ethyl group, a propyl group and a butyl group, a fluoroalkylalkyl group having 1-6 carbon atoms such as a trifluoromethyl group, a perfluoroethyl group, and a perfluoropropyl group, an aryl group having 6-18 carbon atoms such as a phenyl group and a naphthyl group, a furyl group, or a thienyl group;

$R^{25}$ represents an alkyl group having 1-4 carbon atoms or an aryl group having 6-18 carbon atoms for example a phenyl group or a naphthyl group;

n is an integer from 0-200;

$R^{26}$ represents an alkyl group having 1-4 carbon atoms, an aryl group having 6-18 carbon atoms for example a phenyl group or a naphthyl group, or a group shown by the following formula (9):

1.

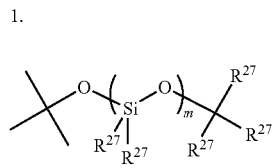

(9)

wherein $R^{27}$ represents an alkyl group having 1-4 carbon atoms, an aryl group having 6-18 carbon atoms for example a phenyl group or a naphthyl group, and m is an integer from 0-100.

As a specific example of the previously mentioned molecule (8), here is presented:

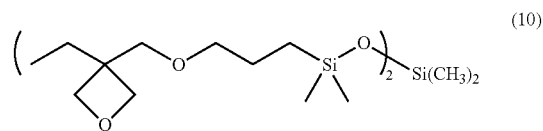

(10)

Those multifunctional rings molecules may also be used for this invention:

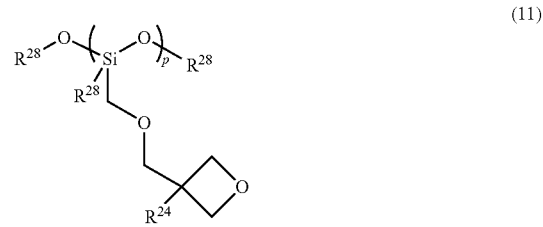

(11)

wherein $R^{28}$ represents an alkyl group having 1-4 carbon atoms or a trialkylsilyl group (wherein each alkyl group individually is an alkyl group having 1-12 carbon atom), for example a trimethylsilyl group, a triethylsilyl group, a tripropylsilyl group, or a tributylsilyl group, $R^{24}$ is the same as defined in the previous formula (8).

And p is an integer from 1-10.

As a specific example of compounds having three or more oxetane rings in the molecule, compound shown by the following formula (12) can be given:

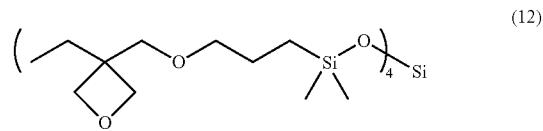

(12)

Further Lactones and lactone derivatives such as spiroorthoesters and spiroorthocarbonates can be used in the present inventions.

Examples of suitable lactones are γ-butyrolactones, β-propiolactone, ε-caprolactone, D-glucono-1,5-lactone, 1,6-dioxaspiro-4,4 nonane-2,7-dione, 4-methyl-3-(1-pyrrolidinyl)-2[5H]-furanone, (5R)-5-[(1S)-1,2-dihydroxyethyl]-3,4-dihydroxyfuran-2(5H)-one, 3a,4,5,7a-tetrahydro-3,6-dimethylbenzofuran-2(3H)-one, 5-methylpentanolide, 5-propylpentanolide, 5-butylpentanolide, 5-pentylpentanolide, 5-hexylpentanolide, 5-heptylpentanolide, 5-pentylpent-2-en-5-olide, Z-2-pentenylpentan-5-olide, 5-pentylpenta-2,4-dien-5-olide.

Furthermore, spirobislactone can also be used when prepared by copolymerisation of epoxy resins with e.g.; 1,6-dioxaspiro-(4,4)-nonane-2,7-dione.

Furthermore, as noted above, it is possible that the cationically curable component of the present invention includes a mixture of the cationically curable compounds described above.

Radically Curable Component

Preferably, the photocurable composition further comprises a radically curable component.

The radically curable component includes at least one radically curable compound that is activated in the presence of an initiator capable of initiating free radical polymerization such that it is available for reaction with other compounds bearing radically curable functional groups.

Examples of free radically curable compounds include compounds having one or more ethylenically unsaturated groups, such as, compounds having (meth)acrylate groups. "(Meth)acrylate" refers to an acrylate, a methacrylate, or a mixture thereof and includes monofunctional monomers containing one ethylenically unsaturated bond in one compound and polyfunctional monomers containing two or more unsaturated bonds in one compound.

Preferably the radically curable component is a (meth) acrylate which is selected from the group consisting of monofunctional, polyfunctional or poly(meth)acrylate monomers.

In one embodiment, the (meth)acrylate is a monofunctional monomer such as (meth)acrylamide, (meth)acryloylmorpholine, isobutoxymethyl(meth)acrylamide, isobornyloxyethyl (meth)acrylate, isobornyl (meth)acrylate, 2-ethylhexyl (meth)acrylate, ethyldiethylene glycol (meth) acrylate, t-octyl (meth)acrylamide, diacetone (meth)acrylamide, lauryl (meth)acrylate, dicyclopentadiene (meth)acrylate, dicyclopentenyloxyethyl (meth)acrylate, dicyclopentenyl (meth)acrylate, N,N-dimethyl(meth)acrylamide, tetrachlorophenyl (meth)acrylate, 2-tetrachlorophenoxyethyl (meth)acrylate, tetrahydrofuryl (meth)acrylate, tetrabromophenyl (meth)acrylate, 2-tetrabromophenoxyethyl (meth)acrylate, 2-trichlorophenoxyethyl (meth)acrylate, tribromophenyl (meth)acrylate, 2-tribromophenoxyethyl (meth)acrylate, 2-hydroxyethyl (meth)acrylate, 2-hydroxypropyl (meth)acrylate, vinylcaprolactam, N-vinylpyrrolidone, phenoxyethyl (meth)acrylate, butoxyethyl (meth)acrylate, pentachlorophenyl (meth)acrylate, pentabromophenyl (meth)acrylate, polyethylene glycol mono(meth) acrylate, polypropylene glycol mono(meth)acrylate, bornyl (meth)acrylate and methyltriethylene diglycol (meth)acrylate and mixtures thereof.

Examples of commercially available monofunctional monomers include SR256 (2(2-ethoxyethoxy ethyl acrylate), SR339 (2-phenoxyethyl acrylate), SR531 (cyclic trimethylolpropane formal acrylate), SR495B (caprolactone acrylate), SR535 (dicyclopentadienyl methacrylate), SR506D (isobornyl acrylate), SR423 (isobornyl methacrylate), SR313A, 313B and 313D ($C_{12}$-$C_{14}$ alkyl (meth)acrylates), all available from Sartomer Co. Inc. and Ciba® Ageflex FM6 (n-hexyl (meth)acrylate available from Ciba Specialty Chemicals).

In another embodiment, the (meth)acrylate is a polyfunctional or poly(meth)acrylate monomer having a functionality of 2 or more. Examples of poly(meth)acrylate monomers include ethylene glycol di(meth)acrylate, dicyclopentenyl di(meth)acrylate, Methylene glycol diacrylate, tetraethylene glycol di(meth)acrylate, tricyclodecanediyldimethylene di(meth)acrylate, tris(2-hydroxyethyl)isocyanurate di(meth) acrylate, tris(2-hydroxyethyl)isocyanurate tri(meth)acrylate, caprolactone-modified tris(2-hydroxyethyl)isocyanurate tri (meth)acrylate, trimethylolpropane tri(meth)acrylate, EO-modified trimethylolpropane tri(meth)acrylate, PO-modified trimethylolpropane tri(meth)acrylate, tripropylene glycol di(meth)acrylate, neopentyl glycol di(meth)acrylate, 1,4-butanediol di(meth)acrylate, 1,6-hexanediol di(meth)acrylate, pentaerythritol tri(meth)acrylate, pentaerythritol tetra(meth)acrylate, polyester di(meth)acrylate, polyethylene glycol di(meth)acrylate, dipentaerythritol penta (meth)acrylate, dipentaerythritol tetra(meth)acrylate, caprolactone-modified dipentaerythritol hexa(meth)acrylate, caprolactone-modified dipentaerythritol penta(meth)acrylate, ditrimethylolpropane tetra(meth)acrylate, EO-modified bisphenol A di(meth)acrylate, PO-modified bisphenol A di(meth)acrylate, EO-modified hydrogenated bisphenol A di(meth)acrylate, PO-modified hydrogenated bisphenol A di(meth)acrylate, EO-modified bisphenol F di(meth)acrylate and mixtures thereof.

The following are examples of commercially available poly(meth)acrylates: SR 295 (pentaerythritol tetracrylate); SR 350 (trimethylolpropane trimethacrylate); SR 351 (trimethylolpropane triacrylate); SR 367 (tetramethylolmethane tetramethacrylate); SR 368 (tris(2-aeryloxy ethyl) isocyanurate triacrylate); SR 399 (dipentaerythritol pentaacrylate); SR 444 (pentaerythritol triacrylate); SR 454 (ethoxylated (3) trimethylolpropane triacrylate); SR 8335 (tricyclodecane dimethanol diacrylate) and SR 9041 (dipentaerythritol pentaacrylate ester) available from Sartomer Co Inc. In one embodiment, the poly(meth)acrylate comprises a difunctional acrylate compound, for example, SR 8335.

Additional examples of commercially available acrylates which may be used in the present invention include Kayarad® R-526 (hexanedioic acid, bis[2,2-dimethyl-3-[(1-oxo-2-propenyl)oxy]propyl]ester), SR 238 (hexamethylenediol diacrylate), SR 247 (neopentyl glycol diacrylate), SR 306 (tripropylene glycol diacrylate), Kayarad® R-551 (Bisphenol A polyethylene glycol diether diacrylate), Kayarad® R-712 (2,2'-Methylenebis[p-phenylenepoly(oxy-ethylene)oxy]diethyl diacrylate), Kayarad® R-604 (2-Propenoic acid, [2-[1, 1-dimethyl-2-[(1-oxo-2-propenyl)oxy]ethyl]-5-ethyl-1,3-dioxan-5-yl]-methyl ester), Kayarad® R-684 (dimethyloltricyclodecane diacrylate), Kayarad® PET-30 (pentaerythritol triacrylate), GPO-303 (polyethylene glycol dimethacrylate), Kayarad® THE-330 (ethoxylated trimethylolpropane triacrylate), DPHA-2H, DPHA-2C, Kayarad® D-310 (DPHA), Kayarad® D-330 (DPHA), DPCA-20, DPCA-30, DPCA-60, DPCA-120, DN-0075, DN-2475, Kayarad® T-1420 (ditrimethylolpropane tetraacrylate), Kayarad® T-2020 (ditrimethylolpropane tetraacrylate), TPA-2040, TPA-320, TPA-330, Kayarad® RP-1040 (pentaerythritol ethoxylate tetraacrylate) (available from Sartomer Co. Inc.); R-011, R-300, R-205 (methacrylic acid, zinc salt, same as SR 634) (available from Nippon Kayaku Co., Ltd.); Aronix M-210, M-220, M-233, M-240, M-215, M-305, M-309, M-310, M-315, M-325, M-400, M-6200, M-6400 (available from Toagosei Chemical Industry Ca, Ltd.); Light acrylate BP-4EA, BP-4PA, BP-2EA, BP-2PA, DCP-A (available from Kyoeisha Chemical Industry Co., Ltd.); New Frontier BPE-4, TEICA, BR-42M, GX-8345 (available from Daichi Kogyo Seiyaku Co., Ltd.); ASF-400 (available from Nippon Steel Chemical Co.); Ripoxy SP-1506, SP-1507, SP-1509, VR-77, SP-4010, SP-4060 (available from Showa Highpolymer Co., Ltd.); NK Ester A-BPE-4 (available from Shin-Nakamura Chemical Industry Co., Ltd.); SA-1002 (available from Mitsubishi Chemical Co., Ltd.); Viscoat-195, Viscoat-230, Viscoat-260, Viscoat-310, Viscoat-214HP, Viscoat-295, Viscoat-300, Viscoat-360, Viscoat-GPT, Viscoat-400, Viscoat-700, Viscoat-540, Viscoat-3000, Viscoat-3700 (available from Osaka Organic Chemical Industry Co., Ltd.).

The radically curable component can be or can comprise a copolymer obtainable by (co)polymerising a monomer comprising at least 1 (meth)acrylate group, preferably at least 2 (meth)acrylate groups. Commerical examples are: fluorinated polyoxetane oligomer with acrylate functionality like Polyfox® PF 3320, PF3305, from Omnova and polybutadiene di (meth)acrylate ($CN_3O_7$, $CN_3O_3$ from Sartomer).

The PolyFox® family of fluorosurfactants includes polymers with a molecular weight greater than 1,000. The PolyFox® polymers are based on ether links—both the polymer backbone linkages and the link between the backbone and the perfluoroalkyl pendant side chains. The PolyFox® fluorosurfactants are synthesized from perfluoroalkyl starting materials with a fully fluorinated carbon chain length of $C_4$ or less. The current products are made with $C_2F_5$ or $CF_3$ perfluoroalkyl side chain structures. The fluorinated polyether is acrylate-terminated. The oxetane rings are opened.

The basic structure of PolyFox® 3320 compound is the following (x+y equals about 20):

An example of a dendritic polymer acrylate suitable for use is a dendritic polyester acrylate compound. The dendritic polyester acrylate compound preferably has an acrylate functionality of at least 12, and more preferably at least 14. Examples of commercially available dendritic polyester acrylates include CN 2301 and CN 2302 (available from Sartomer Co. Inc.). Also available are siloxane acrylates (Wacker Chemie AG).

Structure 1

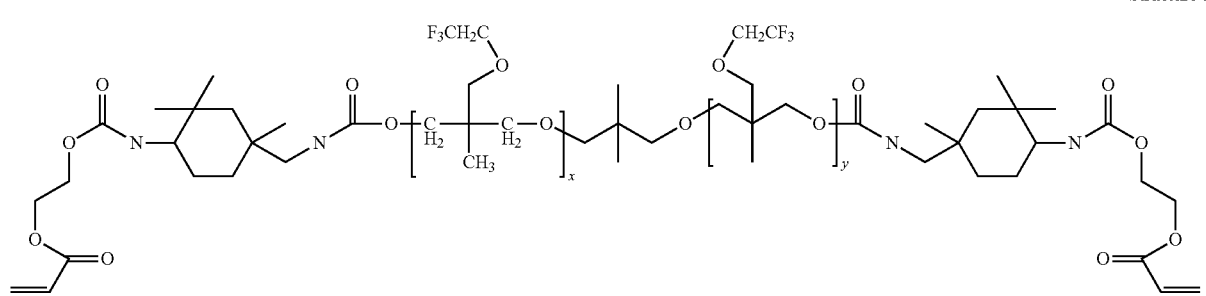

The radically curable compound may also be a (hyperbranched) dendritic polymer acrylate compound. Dendritic polymer acrylate compounds are compounds substantially built up from ester or polyester units, optionally in combination with ether or polyether units to yield a tree-like amorphous structure. These compounds, characterized by having a densely branched backbone and a large number of reactive end groups, are generally made from hydroxy-functional hyperbranched polymer polyols by any of a variety of methods suitable for making acrylate esters including transesterification, direct esterification or reaction with (meth)acryloyl halides.

In a preferred embodiment, the radically curable compound is a (meth)acrylate having a cycloaliphatic structure or a perhydrogenated structure. Preferably the radically curable compound is selected from the group consisting of tricyclodecane dimethanol di(meth)acrylate, hydrogenated bisphenol A di(meth)acrylate, or a compound as defined by the following formulas (13) to (23):

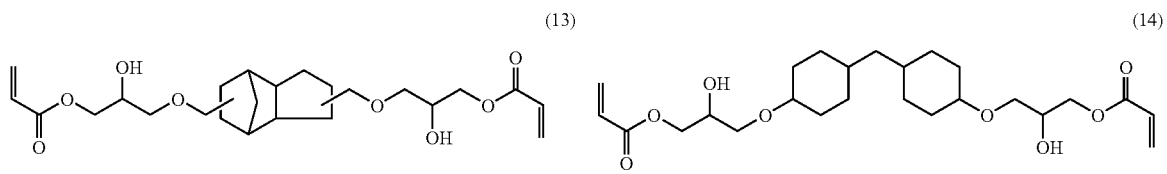

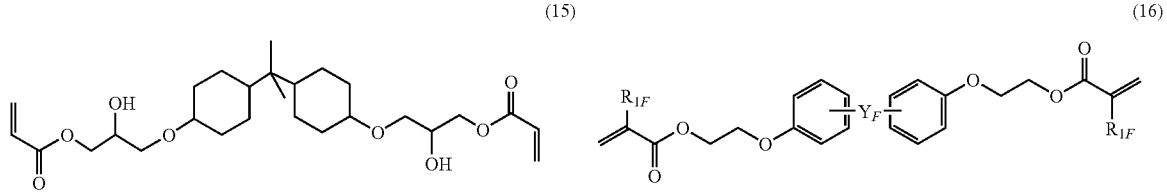

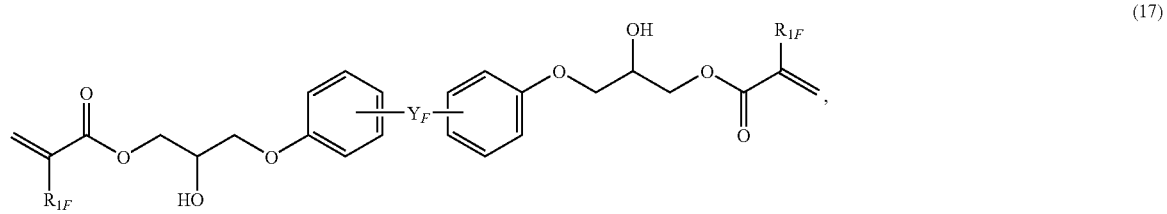

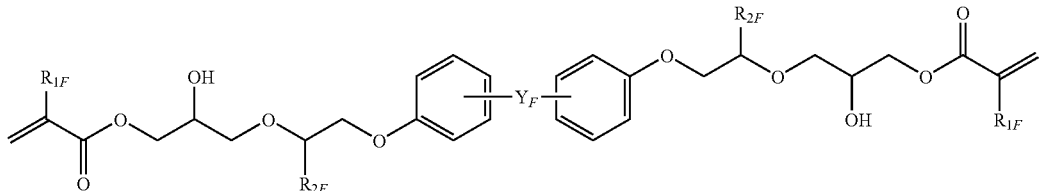
(18)

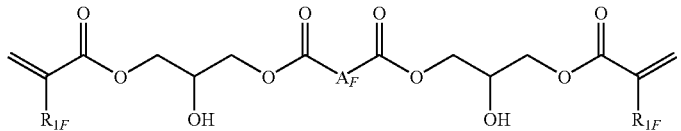
(19)

in which
(a) $R_{1F}$ is a hydrogen atom or methyl,
(b) $Y_F$ is a direct bond, $C_1$-$C_6$ alkylene, —S—, —O—, —SO—, —SO$_2$— or —CO—,
(c) $R_{2F}$ is a $C_1$-$C_8$ alkyl group, a phenyl group in which is unsubstituted or substituted by one or more $C_1$-$C_4$ alkyl groups, hydroxyl groups or halogen atoms, or is a radical of the formula —CH$_2$—OR$_{3F}$ in which
(d) $R_{3F}$ is a $C_1$-$C_8$ alkyl group or phenyl group, and
(e) $A_F$ is a radical selected from the radicals of the formulae

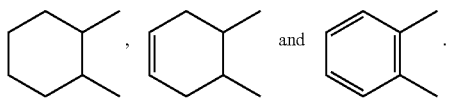

It is possible that the radically curable component of the present invention includes a mixture of the radically curable compounds described above.

In one embodiment, the radically curable component comprises at least one poly(meth)acrylate having a functionality of 2 and a molecular weight within the range from about 200-500. The photocurable composition may contain greater than 5% by weight, preferably greater than 15% by weight, and even more preferably greater than 25% by weight of the poly(meth)acrylate having a functionality of 2 based on the total weight of the photocurable composition. In another embodiment, the radically curable component comprises at most about 60% by weight, more preferably at most about 45% by weight, and even more preferably at most about 40% by weight of the poly(meth)acrylate having a functionality of 2 based on the total weight of the photocurable composition. In yet another embodiment, the poly(meth)acrylate having a functionality of 2 is present in the photocurable composition in the range of from about 5-60% by weight, more preferably from about 10-40% by weight, and even more preferably from about 15-25% by weight based on the total weight of the photocurable composition.

In another embodiment, the radically curable component may further include at least one hyperbranched (dendritic)

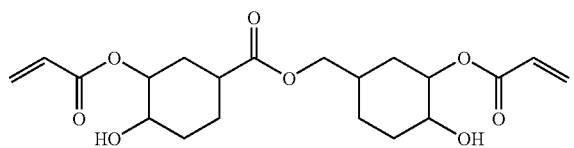
(20)

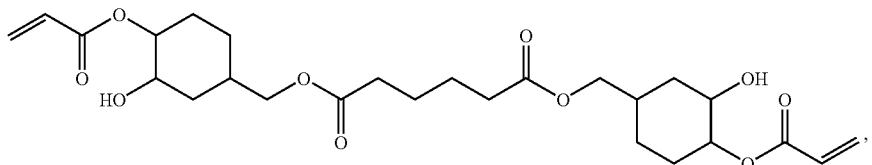
(21)

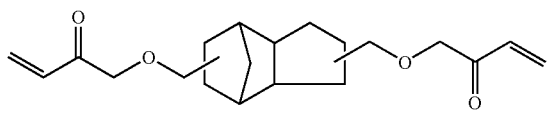
(22)

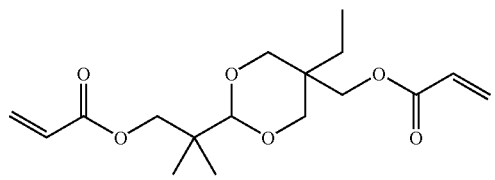
(23)

The above shown compounds are commercially available, from Sartomer.

The radically curable compound may also be an epoxy functionalized compound. Such epoxy functionalized compounds may be obtained by means well known, for example, by reacting a di- or poly-epoxide with one or more equivalents of an ethylenically unsaturated carboxylic acid. An example of such a compound is the reaction product of UVR-6105 with one equivalent of methacrylic acid. Commercially available compounds having epoxy and free-radically active functionalities include the "Cyclomer" series, such as Cyclomer M-100, M-101, A-200 and A-400 available from Daicel Chemical Industries Ltd., Japan, and Ebecryl-3605 and -3700 available from UCB Chemical Corp.

polyester acrylate compound so that the dendritic polyester acrylate is present in the photocurable composition at an amount of at least 1% by weight, preferably at least about 5% by weight, and even more preferably at least about 10% by weight based on the total weight of the photocurable composition. In yet another embodiment, the dendritic polyester acrylate is present in an amount of at most about 40% by weight, preferably at most about 30% by weight, and even more preferably at most about 20% by weight based on the total weight of the photocurable composition. In yet another embodiment, the dendritic polyester acrylate is present in the range of from about 0.01-35% by weight, more preferably from about 0.5-25% by weight and even more preferably from about 1-15% by weight based on the total weight of the photocurable composition.

In yet another embodiment, the radically curable component may further comprise at least one epoxy functionalized compound. When present in the photocurable composition, the epoxy functionalized compound is preferably present at an amount from about 0.01-30% by weight, preferably from about 0.5-25% by weight and even more preferably from about 1-20% by weight based on the total weight of the photocurable composition.

In general the radically curable component is present in an amount of 5 to 80% by weight, preferably 10 to 70% by weight, especially preferred in an amount of 15 to 60% by weight, wherein the percent by weight is based on the total weight of the photocurable composition.

Preferably, the photocurable composition has a viscosity in the range of 5 mPa·s to 10 Pa·s, more preferable between 20 mPa·s and 5 Pa·s, most preferably between 50 mPa·s and 1500 mPa·s measured at 30° C. with a Brookfield Viscometer LVT DVII.

According to a preferred embodiment the photocurable composition according to the present invention comprises a mixture of triaryl sulfonium hexafluorophosphate salt and triaryl sulfonium hexafluoroantimonate salt wherein the amount of triaryl sulfonium hexafluorophosphate salt is equal to or above 50 wt.-% in the photoinitiator composition based on the total weight of the photoinitiator composition.

According to a preferred embodiment of the present invention in case a radically curable component is present, a free-radical photoinitiator is also added to the composition.

Toughening Agents

The photocurable composition of the present invention may also include 0-40% by weight, preferably about 0.01-40% by weight, based on the total weight of the photocurable composition, of one or more toughening agents.

The toughening agent may be a reactive and/or non-reactive core shell type. For example, in one embodiment, the toughening agent which may be added to the photocurable composition includes reactive particles having a crosslinked elastomeric core and a shell containing reactive groups. The reactive particles may be made by methods known to the person skilled in the art. This reference discloses reactive particles that are useful in producing fiber-reinforced plastics, structural adhesives, laminated plastics, and annealing lacquers.

The core of the reactive particles may be composed of polysiloxane, polybutadiene, polybutadiene-co-styrene, amine-terminated polybutadiene, methacrylated polybutadiene, alkyl acrylates, polyorganosiloxane, rubber, poly(ethylene glycol) modified urethane acrylate, polyurethane acrylate polycarbonate, PTFE or other elastomeric material. In one embodiment, the crosslinked core is composed of polysiloxane. In another embodiment, the polysiloxane core is a crosslinked polyorganosiloxane rubber that may include dialkylsiloxane repeating units, where alkyl is a $C_{1-6}$ alkyl. In yet another embodiment, the polysiloxane core includes dimethylsiloxane repeating units.

The shell containing the reactive groups may be composed of poly(styrene-co-acrylonitrile), poly(acrylonitrile), poly (carboxy-functionalized PMMA-co-styrene), polystyrene-co-butyl acrylate, polystyrene, poly(methylmethacrylate-co-maleic anhydride), poly(alkyl methacrylate), poly(styrene-co-acrylonitrile), polystyrene, poly(methylmethacrylate-co-styrene), poly(styrene-co-acrylonitrile), modified vinyl esters, epoxies, PMMA, polyglycidylmethacrylate-co-acrylonitrile, poly(cyclohexanedimethanol terephthalate), thermoplastic resin such as polycarbonate, poly(methylmethacrylate-co-glycidyl methacrylate), poly (methylmethacrylate-co-acrylonitrile-co-divinyl benzene).

The reactive groups of the shell may be epoxy groups, oxetane groups, ethylenically unsaturated groups, and/or hydroxy groups. In one embodiment, the reactive groups may be an oxirane, glycidyl ether, cycloaliphatic epoxies, vinyl ester, vinyl ether, acrylate group, and mixtures thereof.

The reactive particles preferably have an average particle diameter of about 0.01-50 μm, more preferably about 0.1-5 μm, and even more preferably about 0.1 to about 3 μm. Examples of reactive particles that are commercially available include Albidur® EP 2240, silicone-epoxy particles in Bisphenol A epoxy resin; Albidur® VE 3320, silicone-vinyl ester particles in Bisphenol A vinyl ester; and Albidur® EP 5340, silicone-epoxy particles in cycloaliphatic epoxy resin (all available from Hanse Chemie).

In one embodiment, the reactive particles are added to the photocurable composition as a mixture of the reactive particles and a reactive liquid medium containing, e.g., epoxy or ethylenically unsaturated groups. For example, the reactive organosiloxane particles are dispersed in bisphenol A glycidyl ether for Albidur® EP 2240, in bisphenol A vinyl ester for Albidur® VE 3320 and in cycloaliphatic epoxide for Albidur® EP 5340.

The amount of the reactive particles added to the photocurable composition may be varied depending on the cationically curable component and radically curable component. When present, the photocurable composition may contain at least about 0.5% by weight, more preferably at least about 1% by weight, and even more preferably at least about 1.5% by weight based on the total weight of the photocurable composition. In another embodiment, the reactive particles present is at most about 40% by weight, more preferably at most about 15% by weight, and even more preferably at most about 10% by weight based on the total weight of the photocurable composition. In yet another embodiment, the reactive particles are present in a range of from about 0.01-40% by weight, preferably from about 0.5-15% by weight, and even more preferably from about 1-5% by weight of the reactive particles based on the total weight of the photocurable composition.

Other toughening agents which may be added to the photocurable composition in addition to or in lieu of the reactive particles include one or more hydroxyl-containing compounds. The hydroxyl-containing compound(s) have a functionality of at least 1 and more preferably at least 2, and are free of any groups which inhibit the curing reaction. The hydroxyl-containing compound may be an aliphatic or aromatic hydroxyl-containing compound. Examples include polyether polyols, polyester polyols, hydroxyl and hydroxyl/epoxy functionalized polybutadiene, 1,4-cyclohexanedimethanol, polycaprolactone dials and triols, ethylene/butylene polyols, polyurethane polyols and monohydroxyl functional monomers.

In one embodiment, the hydroxyl-containing compound is a polytetramethylene ether glycol ("poly THF"). The poly THF preferably has a molecular weight from about 250 to about 2500 and may be terminated with hydroxy, epoxy, or ethylenically unsaturated group(s). Commercially available poly THF's' include Polymeg® poly THF's, for example, Polymeg® 1000, which is a linear diol with a nominal molecular weight of 1000 (Penn Specialty Chemicals). In another embodiment, the hydroxyl-functional compound is a caprolactone based oligo- or polyester, for example, a trimethylolpropane-triester with caprolactone, such as Tone® 301 (Dow Chemical Co.). In another embodiment, the hydroxy-functional compound is a polyester, for example k-flex 188 (from Kings Industries) or Simulsol TOMB from SEPPIC.

When present, the total amount of the hydroxyl-containing compound which may be added to the photocurable composition may generally be from about 0.01-40% by weight and preferably from about 0.5-20% by weight based on the total weight of the photocurable composition.

Another type of toughener is a class of oligomers or polymers which are compatible with the cationically and radically curable components of the photocurable composition.

Compatible means that this type of toughener is soluble in the curable monomers and does not generate macroscopic phase separation prematurely during storage at room temperature (20° C.) prior to use.

Preferred are compatible block copolymers, which dissolve in the cationically curable component, form self ordered structures and exhibit microscopic phase separation upon curing when investigated by X-ray or neutron scattering or SEM (scanning electron microscsopy) or TEM (transmission electron microscopy). Preferably the structures have miscelle domains.

This type of self ordering block copolymer comprises one or more block copolymers having at least one block composed of methyl methacrylate. Preferred are block copolymers which are constituted of three blocks of linear chains covalently bonded to one another, and which exhibit a microscopic phase separation. Said family may comprise S-B-M and the M-B-M-triblock copolymers. S-B-M triblocks are, in particular, constituted of polystyrene (PS), 1,4-polybutadiene (PB) and poly(methylmethacrylate) (PMMA), being preferably syndiotactic, whereas M-B-M-triblocks are symmetric block copolymers constituted of a center block of a poly (butylacrylate) or a diene and two side blocks of poly(methylmethacrylate) (PMMA).

As regards the S-B-M triblock, M is preferred composed of methyl methacrylate monomers or comprises at least 50% by mass of methyl methacrylate, preferably at least 75% by mass of methyl methacrylate. The other monomers constituting the M block can be acrylic or non-acrylic monomers and may or may not be reactive. The term "reactive monomer" is understood to mean: a chemical group capable of reacting with the functional groups of the compound, or with the chemical groups of the acrylate-containing compound or with the chemical groups of the hardeners. Non-limiting examples of reactive functional groups are: oxirane functional groups, oxetane functional groups, (meth)acrylate functional groups, hydroxyl functional groups, amine functional groups or carboxyl functional groups. The reactive monomer can be (meth) acrylic acid or any other hydrolysable monomer resulting in these acids. Among the other monomers which can constitute the M block, non-limiting examples are glycidyl methacrylate or tert-butyl methacrylate. M is advantageously composed of syndiotactic PMMA to at least 60%. The M block of the S-B-M triblock can be identical or different.

The Tg of B is advantageously less than 0° C. and preferably less than −40° C.

Nanostrength® E20, Nanostrength® E21 and Nanostrength® E 40, Nanostrength® A123, Nanostrength®A250 and Nanostrength®A012 products are representative of triblockcopolymers of the S-B-M type obtainable from the company Arkema, France.

As regards the M-B-M triblock, M is composed of methyl methacrylate monomers or comprises at least 50% by weight of methyl methacrylate, preferably at least 75% by weight of methyl methacrylate. The other monomers constituting the M block can be acrylic or non-acrylic monomers and may or may not be reactive. The term "reactive monomer" is understood to mean: a chemical group capable of reacting with the functional groups of the cationic compound or with the chemical groups of the acrylate-containing compound or with the chemical groups of the hardeners. Non-limiting examples of reactive functional groups are: oxirane functional groups, oxetane functional groups, (meth)acrylate functional groups, hydroxyl functional groups, amine functional groups or carboxyl functional groups. The reactive monomer can be (meth) acrylic acid or any other hydrolysable monomer resulting in these acids. Among the other monomers which constitute the M-block are e.g. glycidyl methacrylate or tert.-butyl methacrylate. M is advantageously composed of syndiotactic PMMA to at least 60%. The two M-blocks of the M-B-M triblock can be identical or different. They can also be different in their molar mass but composed of the same monomers.

The Tg of B is advantageously less than 0° C. and preferably less than −40° C.

The above-mentioned block-copolymers are preferably present in the photocurable compositions in amounts of 0.5 to 20% by weight, more preferably in amounts of 1 to 15% by weight and in particular in amounts of 1.5 to 10% by weight, based on the total weight of the photocurable composition.

According to a preferred embodiment of the present invention the photocurable composition contains a toughening agent which comprises one or more block copolymers having at least one block composed of methyl methacrylate.

Other Optional Components

The photocurable composition of the present invention may also include other components, for example, stabilizers, modifiers, antifoaming agents, leveling agents, thickening agents, flame retardants, antioxidants, pigments, dyes, fillers, nano-fillers having a mean average particle size of 3 to 700 nanometers, and combinations thereof.

Stabilizers which may be added to the photocurable composition to prevent viscosity build-up during usage include butylated hydroxytoluene ("BHT"), 2,6-di-tert-butyl-4-hydroxytoluene, hindered amines, e.g., benzyl dimethyl amine ("BDMA"), and boron complexes. Other examples of stabilizers are ammonia, substituted ammonia or salt of metal of group IA/IIA. If used, the stabilizers may constitute from about 0.001% to about 5% by weight based on the total weight, preferably from 0.001% to 2% by weight of the photocurable composition.

Fillers, including inorganic or organic, powdered, flaky or fibrous materials, may also be added. Examples of inorganic fillers include mica, glass or silica, calcium carbonate, barium sulfate, talc, glass or silica bubbles, zirconium silicate, iron oxides, glass fiber, asbestos, diatomaceous earth, dolomite, powdered metals, titanium oxides, pulp powder, kaoline, modified kaolin, hydrated kaolin metallic fillers, ceramics and composites. Examples of organic fillers include polymeric compounds, thermoplastics, core-shell, aramid, kevlar, nylon, crosslinked polystyrene, crosslinked poly(methyl methacrylate), polystyrene or polypropylene, crosslinked polyethylene powder, crosslinked phenolic resin powder, crosslinked urea resin powder, crosslinked melamine resin powder, crosslinked polyester resin powder and crosslinked epoxy resin powder. Both the inorganic and organic fillers can optionally be surface treated with various compound-coupling agents. Examples include methacryloxy propyl trimethoxy silane, beta-(3,4-epoxycyclohexyl)ethyl trimethoxy silane, gamma-glycidoxy propyl trimethoxy silane and methyl triethoxy silane. Mixtures of inorganic and organic fillers may also be used.

Further examples of preferred fillers are micro crystalline silica, crystalline silica, amorphous silica, alkali alumino silicate, feldspar, wollastonite, alumina, aluminum hydroxide, glass powder, alumina trihydrate, surface treated alumina trihydrate, and alumina silicate. Each of the preferred fillers is commercially available. The most preferred filler materials are inorganic fillers, such as mica, Imsil, Novasite, amorphous silica, feldspar, and alumina trihydrate. These fillers preferably are transparent to UV light, have a low tendency to refract or reflect incident light and provide good dimensional stability and heat resistance. Nano fillers, such as exfoliated clays (nano clays), nano mica, aluminum borate whiskers, nano barium sulphate (Nanofine, available from Solvay), silica nanoparticules dispersed in UV-curable monomers (Nanopox and Nanocryl range of materials from Nanoresins), alumina nanoparticules dispersed in UV-curable monomers (Nanobyk from Byk Chemie) may also be used.

The filler and nanofiller to be used for the resin composition for stereolithography according to the present invention must also satisfy the requirements that it does not hinder cationic or radical polymerizations and the filled SL composition must have a relatively low viscosity suitable for the stereolithography process. The fillers and nanofillers may be used alone or as a mixture of two or more fillers depending upon the desired performance. The fillers and nanofillers used in the present invention may be neutral, acidic or basic, with slightly basic being preferred. The filler particle size may vary depending on the application and the desired resin characteristics. It may vary between 50 nanometers and 50 micrometers. The nanofillers particle size may vary between 3 and 500 nanometers. Dispersants may be used to ensure good dispersion of these nanofillers.

If present, the content of fillers in the photocurable composition may generally be about 0.5% by weight to about 30% by weight based on the total weight of the photocurable composition.

The photocurable compositions of the present invention can be prepared in a known manner, for example, by premixing individual components and then mixing these premixes, or by mixing all of the components together using customary devices, such as stirred vessels. In one embodiment, the mixing is carried out in the absence of light and, if desired, at slightly elevated temperatures ranging from about 30° C. to about 60° C.

In one embodiment, the photocurable composition of the present invention is prepared by mixing from about 35-80% by weight of the cationically curable component, from about 15-60% by weight of the radically curable component, from about 0.1-10% by weight of cationic photoinitiator composition according to the present invention, from 0-10% by weight of the free radical photoinitiator, and from 0-40% by weight of the toughening agent where the % by weight is based on the total weight of the photocurable composition. In another embodiment, the photocurable composition is produced by mixing from about 45-70% by weight of the cationically curable component comprising a hydrogenated bisphenol epoxy-containing compound and an oxetane compound, greater than 25-40% by weight of the radically curable component comprising at least one poly(meth)acrylate having a functionality of 2, from about 0.5-8% by weight of the cationic photoinitiator composition, from about 0.5-4% by weight of the free radical photoinitiator, and from 0-40%, preferably from about 0.01-40% by weight of the toughening agent where the % by weight is based on the total weight of the photocurable composition.

According to a preferred embodiment of the present invention the photocurable composition is a liquid composition comprising a) an epoxy-containing compound as defined before, preferably a cycloaliphatic epoxy compound and/or an epoxy compound with a hydrogenated aromatic backbone such as hydrogenated bisphenol A diglycidyl ether;

b) a (meth)acrylate as defined herein before, preferably a (meth)acrylate having two (meth)acrylate groups within the molecule, more preferably selected from the group as defined by the formulas (13) to (23);

c) an oxetane as defined herein before;

d) a photoinitiator composition according to the invention; and e) optionally a (meth)acrylate having 3 or more (meth)acrylate groups within the molecule.

According to a further embodiment the photocurable composition is a jettable composition comprising at least an oxetane as defined herein before as well as the photoinitiator composition according to the invention and wherein the photocurable composition has a vicosity from 10 to 500 mPa·s at 30° C., measured with a Brookfield Viscosimeter LVT DVII.

The photocurable compositions can be polymerized by irradiation with actinic light, for example by means of electron beams, X-rays, UV or V is light, preferably with radiation in the wavelength range of 280-650 mm. Preferably the polymerization is carried by irradiation with monochromatic light. Particularly suitable are laser beams of HeCd, argon ion or nitrogen and also metal vapour and NdYAG lasers. This invention is extended throughout the various types of lasers existing or under development that are to be used for the solid imaging (stereolithography) process, e.g. solid state, argon ion lasers, etc, as well as to non-laser based irradiations. The person skilled in the art is aware that it is necessary, for each chosen light source, to select the appropriate photoinitiator and, if appropriate, to carry out sensitization. It has been recognized that the depth of penetration of the radiation into the composition to be polymerized, and also the operating rate, are directly proportional to the absorption coefficient and to the concentration of the photoinitiator. In stereolithography it is preferred to employ those photoinitiators which give rise to the highest number of forming free radicals or cationic particles and which enable the greatest depth of penetration of the radiation into the compositions which are to be polymerized.

Therefore a further embodiment of the present invention is a process for producing a three dimensional article comprising:

(a) forming a first layer of the photocurable composition according to the present invention on a surface;

(b) exposing the layer imagewise to irradiation to form an imaged cross-section;

(c) forming a second layer of the photocurable composition in the previously exposed imaged cross-section;

(d) exposing the second layer from step (c) imagewise to irradiation to form an additional imaged cross-section; and (e) repeating steps (c) to (d) a sufficient number of times in order to built up the three-dimensional article.

The irradiation in step (b) can be carried out by any of the above-mentioned sources. The irradiation must be of sufficient intensity to cause substantial curing of the layer in the exposed areas. Likewise it is desired that the irradiation in step (d) is of sufficient intensity to cause adhesion of the previously exposed imaged cross section.

The photocurable composition used in step (c) may be the same photocurable composition as used in step (a) or may be different from the photocurable composition used in step (a).

The three-dimensional articles produced can be used in various applications, for example, the aerospace industry and the investment casting industry, or for medical applications.

In principle, any stereolithography machine may be used to carry out the inventive method. Stereolithography equipment is commercially available from various manufacturers. Table I lists examples of commercial stereolithography equipment available from 3D Systems Corp. (Valencia, Calif.).

TABLE A

| MACHINE | WAVELENGTH (nm) |
|---|---|
| SLA ® 250 | 325 |
| SLA ® 500 | 351 |
| SLA ® 3500 | 355 |
| SLA ® 5000 | 355 |
| SLA ® 7000 | 355 |
| Viper si2 ® | 355 |
| Viper Pro V ® | 355 |

Most preferably, the stereolithography process for producing a three-dimensional article from the photocurable composition of the present invention includes preparing the surface of the composition to form the first layer and then recoating the first layer and each successive layer of the three-dimensional article with a Zephyr® recoater (3D Systems Corp., Valencia, Calif.), or an equivalent thereof.

The photocurable composition according to the present invention can be cured rapidly in a liquid-based solid imaging process to produce an article for use in medical applications having a high green strength, toughness, dimensional accuracy and minimal distortion.

Although the photocurable composition of the present invention is preferably used in a stereolithography process, it may also be used in coatings, encapsulation, barriers layers to moisture or oxygen ingress into sensitive electronic components or three-dimensional jet printing or other rapid prototyping techniques to produce a three dimensional article.

Therefore a further embodiment of the present invention is a process for producing a three dimensional article by jet printing comprising the steps of:
(a') applying droplets of the photocurable composition according to the present invention at targeted locations on a substrate;
(b') exposing the droplets to electromagnetic radiation to cure the droplets in the exposed areas;
(c') repeating steps (a') and (b') a sufficient number of times in order to build up the three dimensional article.

In jet printing, successive droplets of the photocurable composition are applied (e.g. using an ink jet print head such as a piezoelectric jet printing head) at targeted locations on a substrate and irradiated by exposing the droplets to electromagnetic radiation to cure the composition and build up a three dimensional article of a desired shape. In general, the droplets are deposited in accordance with the desired shape which is stored in a computer file, for example a CAD file. In order to produce tough deposits, it is desirable to use photocurable compositions having resin viscosities around 500 mPa·s. However for best jettability using commercial printheads, such as Novajet from Spectra, the viscosity of the photocurable composition has to be below 30 mPa·s, for maximum stable printhead temperature operation at 80° C., preferably at 70° C., and more preferably at 50° C. Under these temperature conditions, it is crucial that the formulated resin is stable and does not polymerise in the printhead, prior to jetting. The photoinitiator composition described in this invention can be chosen very well to fit with the required stable inkjet printhead performance. Preferably such photoinitiator compositions are combined with the oxetanes which are required diluents to reduce the viscosity to acceptable levels for successful, stable jetting. Even, very simple formulations with epoxy and oxetane components, optionally with polyols, are found to be useful to form jetted tough, hard deposits.

According to a preferred embodiment of the present process the substrate is preferably selected from the group consisting of paper, textiles, tiles, printing plates, wall paper, plastic, powder, paste or a reactive resin which is liquid or an already partly cured resin which is liquid.

Preferably the photocurable composition is exposed to electromagnetic radiation pixel by pixel, line by line, layer by layer.

Preferably, the electromagnetic radiation employed is UV light, microwave radiation or visible light.

The same sources of electromagnetic irradiation as already mentioned before can be used. In particular irradiation within a wavelength range of 280 to 650 nm is preferred.

The photocurable composition used in a subsequent step may be different from the photocurable composition used in a former step.

Alternatively, it is possible to deposit the photocurable composition of the present invention onto a powder. The powder may be spread as a thin layer onto the substrate and the photocurable composition jet deposited onto the powder at desired locations in a desired pattern. The pattern may then be cured by exposing the photocurable composition to electromagnetic irradiation. A further layer of powder may then be placed on top of the first layer and the process is repeated to build up the three dimensional article. Any powder may be removed after the three dimensional article has been built. A final heat and/or radiation cure may be provided for the three dimensional article after the powder which has not been ingressed with the liquid photocurable composition is removed. The photocurable composition is preferably fully integrated with the powder such that there are substantially no voids left between the original powder particles which particularly provide high strength parts.

In another embodiment, the powder contains a reactive component that can react either with the photocurable composition or is facilitated by the photocurable composition to react with itself. The powder may contain organometallic polymers, oligomers, or monomers. Examples include polyacrylic acid, poly(acrylonitrile-co-butadiene, poly(allylamine), polyacrylic resins with functional acrylate groups, polybutadiene, epoxy functionalized butadienes, poly(glycidyl(meth)acrylate), poly THF, polycaprolactone diols, HEMA, HEA, maleic anhydride polymers such as styrene-maleic anhydride, polyvinylbutryals, polyvinyl alcohol, poly(4-vinylphenol), copolymers/blends of these compounds, and any of these compounds endcapped with epoxy, vinyl ether, acrylate/methacrylate, hydroxy, amine or vinyl moieties. The powder may further contain an organic or an inorganic filler, a pigment, a nanoparticle, a dye, and/or a surfactant.

In other embodiments, the powder is preferably a thermoplastic powder, for example PMMA, BUTVAR, Polycarbonate, PEEK, etc.

In one embodiment, the three dimensional article produced from the photocurable composition of the present invention is used as a foundry pattern in investment casting. In investment casting, a disposable foundry pattern produced from the photocurable composition of the present invention is used to produce a mold in which parts can be cast. The mold is built up around the foundry pattern by a well known process the details of which differ depending upon the type of metal to be cast in the mold. In general, and using the casting of ferrous alloys to illustrate the investment casting process, the foundry pattern is coated with, i.e., invested in, a refractory slurry, for example an aqueous ceramic slurry, which is drained of excess water to form a coating, and the coating is then stuccoed with fine ceramic sand. This step is usually repeated several times (10 to 20 layers are not uncommon) after the first coating is dry. The invested foundry pattern is then placed in an open ended metal container which is filled with a coarse slurry of ceramic back-up material which hardens. The foundry pattern which is invested in the ceramic is then placed into a furnace or autoclave causing the foundry pattern to be melted or burned out of the resulting mold. Removal of the foundry pattern leaves a cavity in the mold corresponding in shape and dimension to the final part, although the foundry pattern (and therefore the cavity) can be slightly larger to compensate for shrinkage or machining of the part which is produced by the subsequent casting operation. Molten metal is introduced into the mold cavity and solidified by cooling. After solidification, the ceramic mold is broken away to release the finished part. While metal castings are primarily contemplated, any liquid material which solidifies may be cast in this manner, e.g., plastic or ceramic compositions.

Sensitive alloys can be cast in molds produced by the stereolithographically-made foundry pattern. Furthermore, complex foundry patterns can be accurately produced. Finally, it has been found that the foundry patterns have a low ash content (<0.05%), retain their accuracy and rigidity over time, making them ideal for casting reactive metals.

Use of the Photoinitiator Composition

The photoinitiator composition as described herein may be used as a photoinitiator.

Preferably, it is used in a photocurable composition to increase the green strength and/or thermal stability.

Other applications where the photocurable composition and/or the cationic photoinitiator composition of the present invention may be used are in adhesives, coatings, such as a photoimageable coating like a photoresist, or a coating for optical fibers or lenses, sealants such as a sealing for light emitting diodes, paints, inks or varnishes or any other application, process or method where a shelf-stable photocurable composition having stable mechanical properties on curing is desired. Furthermore the photocurable composition and/or the cationic photoinitiator composition of the present invention may be used in stereolithographic processes, inkjet printing processes, rapid prototyping processes, soldermask processes and rapid manufacturing processes.

Rapid Manufacturing

Rapid manufacturing is a technique for manufacturing solid objects by the sequential delivery of energy and/or materials to specified points in a space to produce that part. Current practice is to control the manufacturing process by a computer using a mathematical model created with the aid of a computer. Rapid manufacturing done in parallel batch production provides a large advantage in speed and cost overhead compared to alternative manufacturing techniques such as laser ablation or die casting.

Green Strength/Green Model

The term "green model" as used herein means a three-dimensional article initially formed by the stereolithography process of layering and photocuring, where typically the layers are not completely cured. This permits successive layers to better adhere by bonding together when further cured.

The term "Green strength" is a general term for mechanical performance properties of a green model, including modulus, strain, strength, hardness, and layer-to-layer adhesion. For example, green strength may be reported by measuring flexural modulus (ASTM D 790). An article having low green strength may deform under its own weight, or may sag or collapse during curing.

The green model is washed in isopropanol and dried. The dried green model is postcured with UV radiation in a postcure apparatus (PCA®, 3D Systems) for about 60-90 minutes. "Postcuring" is the process of reacting the green model to further cure the partially cured layers. A green model may be postcured by exposure to heat, actinic radiation, or both.

EXAMPLES

Raw Materials Used

| Trade Name | Source | Chemical Name |
|---|---|---|
| Uvacure 1500 | Cytec | 3,4-epoxycyclohexylmethyl-3',4'-epoxycyclohexane-carboxylate |
| DER332 | Dow Chemicals | Bisphenol A diglycidyl ether |
| Epalloy 5000 | CVC Chemicals | Hydrogenated bisphenol A diglycidyl ether |
| Erisys GE 30 | CVC chemicals | Trimethylolproprane triglycidyl ether |
| OXT-101 | Toagosei | 3-ethyl-3-hydroxymethyl oxetane |
| UVR 6000 | Dow | 3-ethyl-3-hydroxymethyl oxetane |
| SR833S | Sartomer Co. | Tricyclodecanedimethanol diacrylate |
| SR 499 | Sartomer Co. | Ethoxylated 6 trimethylolpropane triacrylate |
| SR399 | Sartomer Co. | Dipentaerythrytol pentacrylate |
| CN2301 | Sartomer Co. | Hyperbranched polyester acrylate oligomer |
| Arcol Polyol LG650 | Bayer | Propoxylated glycerol |
| Albidur EP 2240 | Nano Resins | Dispersion of silicone-elastomer in epoxy resin |
| Tego Rad 2100 | Tego Chemie | Crosslinkable silicone acrylate |
| UVI-6976 | Dow Chemicals Company | Mixture of PhS—($C_6H_4$)—$S^+Ph_2SbF_6^-$ and $Ph_2S^+$—($C_6H_4$)S($C_6H_4$)—$S^+Ph_2$—$(SbF_6^-)_2$ |
| UVI-6992 | Dow Chemicals Company | Mixture of PhS—($C_6H_4$)—$S^+$—$Ph_2PF_6^-$ and $Ph_2S^+$—($C_6H_4$)—S—($C_6H_4$)—$S^+$ $Ph_2(PF_6^-)_2$ |
| Esacure 1064 | Lamberti | Mixture of PhS—($C_6H_4$)—$S^+$—$Ph_2PF_6^-$ and $Ph_2S^+$—($C_6H_4$)—S—($C_6H_4$)—$S^+$ $Ph_2(PF_6^-)_2$ |
| Rhodorsil 2074 | Rhodia | (tolylcumyl)iodonium tetrakis(pentafluorophenyl) borate |
| Irgacure 250 | Ciba Specialty Chemicals | (4-methylphenyl), [4-(2-methylpropyl phenyl]iodonium hexafluorophosphate |
| Irgacure 184 | Ciba Specialty Chemicals | 1-hydroxycyclohexyl phenyl ketone |
| Nanostrength AFX E21 | Arkema | Polystyrene-polybutadiene-polymethylmethacrylate block copolymer |

Manufacture of the Compositions and Solid Specimens

Step 1: Preparation of the Compositions

The compositions described in the following examples are prepared by stirring the components at 20° C., until an homogeneous composition is obtained.

The at least two cationic photoinitiators can either be added to the composition individually, or can be mixed together separately, prior to being added to the rest of the previously mixed components.

Step 2: Preparation of the Specimens

Mechanical properties on cationically curable systems are determined on specimens cured by UV irradiation for 90 min in a silicon mold inside a Post-Curing Apparatus (3D Systems).

The mechanical properties of hybrid composition (radically and cationically curable compositions) are evaluated on specimens fabricated using a SLA-7000 (3D Systems) and post cured for 90 min in a Post-Curing Apparatus (PCA®, 3D Systems) to ensure specimens are fully cured.

The specimens for green flexural modulus are fabricated using a SLA-350 (3D Systems). Green specimens are wiped cleaned without use of solvent and are not subject to full cure in the Post-Curing Apparatus.

Testing Procedures

Photospeed

The photosensitivity of the compositions is determined on so-called window panes. In this determination, single-layer test specimens are produced using different laser energies, and the layer thicknesses are measured. The plotting of the resulting layer thickness on a graph against the logarithm of the irradiation energy used gives the "working curve". The slope of this curve is termed Dp (depth of Penetration, in mils [25.4 μm]). The energy value at which the curve passes through the x-axis is termed Ec (Critical Energy, in $mJ/cm^2$). For each example described, the authors have chosen to report the energy [E4 in $mJ/cm^2$] required to fully polymerise a 0.10 mm layer.

Mechanical Testing

Mechanical testing of fully cured parts is performed according to ISO standards. Specimens are conditioned 3-5 days at 23° C. and 50% RH prior to testing.

|  | ISO standard |
|---|---|
| Flexural properties Maximum strength, modulus | 178 |
| Bend Notched Impact Resistance Fracture toughness (G1C), stress intensity coefficient (K1C) | 13586 |

Green Strength

The green strength is determined by measuring the flexural modulus at 1 mm deflexion on a green specimen 10 min and 60 min after fabrication. The green test specimen is a 6.25×2.6×70 mm bar. The distance between the supports during the deflexion test is 40 mm and the cross-head speed during the test is 10 mm/min.

Viscosity

The viscosity of the liquid mixtures is determined using a Brookfield Viscometer LVT DVII (spindle SC4-21 or spindle SC4-18) at 30° C.

Thermal Stability of Compositions

The thermal stability of a photocurable composition can be determined by following the viscosity at 30° C. over time. For practical reasons, in many applications, it is desired that the composition remains stable in viscosity for an extended period of time, and that once active species are present in the mixture, that the increase in viscosity is as slow as possible.

The thermal stability of a composition is defined as the increase in viscosity in centipoise per hour (mPa·s/h), upon storage of this composition at 65° C. for an extended period of time. The viscosity is periodically determined at 30° C. The storage period can vary from 1 h to 960 h.

Method for Defining the Thermal Stability of Cationic Photoinitiators

A cationically curable composition CC is used as a reference for determining the thermal stability of cationic photoinitiators. Cationic photoinitiators, according to this invention, are classified as (A) or (B) depending to their thermal stability in cationic curable composition CC.

| Components | Cationically curable composition CC |
|---|---|
| Uvacure 1500 | 52.80 wt.-% |
| OXT-101 | 47.20 wt.-% |
| Total weight % | 100 |

A composition containing from 90 to 99.9 wt % of cationically curable composition CC and 0.01 to 10 wt % of a cationic photoinitiator is stored at 65° C. degree and the viscosity is periodically measured at 30° C.

Under these conditions, a thermally stable photoinitiator (A) is defined as providing the cationically curable composition CC with thermal stability below 0.40 mPa·s/h over a period of 144 h of storage time at 65° C. A less thermally stable photoinitiator (B) is defined as providing cationic curable composition CC with thermal stability at 0.40 mPa·s/h or higher over a 144 h period of storage time at 65° C.

In general when compositions containing a mixture of cationic photoinitiators (A) and (B) are considered, one can calculate the expected thermal stability (T.S. calc.) of a composition containing both (A) and (B), according to the formula F1, considering that no synergistic effect occurs:

$$T.S.\ calc.=Xa/100*T.S.a+Xb/100*T.S.b \qquad \text{(formula F1)}$$

T.S.a: thermal stability of a photocurable composition containing (A)

T.S.b: thermal stability of a photocurable composition containing (B)

Xa=weight % of photoinitiator (A) in the photocurable composition/(weight % of photoinitiator (A)+weight % of photoinitiator (B) in the photocurable composition)*100

Xb=weight % of photoinitiator (B) in the photocurable composition/(weight % of photoinitiator (A)+weight % of photoinitiator (B) in the photocurable composition)*100 By definition, Xb+Xa=100.

It is demonstrated that the photocurable compositions containing a photoinitiator composition comprising (A) and (B) are far more thermally stable than an ideal mixing would have predicted and that a synergistic effect is observed.

It could be demonstrated that mechanical properties are not significantly affected by the use of a photoinitiators composition comprising (A) and (B). It could even be demonstrated that an improvement of the overall balance of properties is observed.

Series 1: Cationic Curable Compositions

TABLE 1

| | Comparative Ex. 1 | Comparative Ex. 2 | Comparative Ex. 3 | Comparative Ex. 4 |
|---|---|---|---|---|
| Components | | | | |
| Cationic curable composition CC | 97.3 | 98.6 | 97.3 | 97.3 |
| Irgacure 250 | 2.7 | | | |
| rhodorsil 2074 | | 1.4 | | |
| UVI-6976 | | | 2.7 | |
| Esacure1064 | | | | 2.7 |
| Total weight % | 100 | 100 | 100 | 100 |
| Viscosity at 30° C., upon storage at | | | | |

TABLE 1-continued

| | Comparative Ex. 1 | Comparative Ex. 2 | Comparative Ex. 3 | Comparative Ex. 4 |
|---|---|---|---|---|
| 65° C. (mPa · s) | | | | |
| 0 hour | 35.7 | 33.6 | 33.7 | 33.9 |
| 1 hour | 70.8 | | | |
| 8 hours | | solid | | |
| 72 hours | | | 67.1 | |
| 144 hours | | | | 38.1 |
| Thermal stability at 65° C. (mPa · s/h) | 35 | >1000 | 0.46 | 0.029 |
| Storage period (h) | 1 | 8 | 72 | 144 |

Photoinitiator (A): Esacure 1064
Photoinitiator (B): Irgacure 250, Rhodorsil 2074, UVI-6976

TABLE 2

| | Comparative Ex. 5 | Ex. 6 | Ex. 7 | Ex. 8 | Comparative Ex. 9 |
|---|---|---|---|---|---|
| Components | | | | | |
| Cationic curable composition CC | 97.3 | 97.3 | 97.3 | 97.3 | 97.3 |
| UVI-6976 | 2.7 | 2.0 | 1.4 | 0.7 | 0 |
| Esacure1064 | 0 | 0.7 | 1.4 | 2.0 | 2.7 |
| Total weight % | 100 | 100 | 100 | 100 | 100 |
| Xa (%) | 0 | 26 | 50 | 74 | 100 |
| Viscosity at 30° C., upon storage at 65° C. (mPa · s) | | | | | |
| 0 days | 33.7 | / | 33.7 | 33.9 | 33.9 |
| 6 days | 782 | / | 80.2 | 47.4 | 38.1 |
| Thermal stability at 65° C. (mPa · s/h) | 5.2 | / | 0.32 | 0.094 | 0.029 |
| Calculated Thermal stability at 65° C. - T.S. calc (mPa · s/h) | / | 3.85 | 2.61 | 1.37 | / |
| Storage period (h) | 144 | 144 | 144 | 144 | 144 |
| Mechanical properties of cured specimens | | | | | |
| Flexural Modulus (MPa) | 3102 | 2735 | 3536 | 3599 | 3347 |
| K1C (MPa · m$^{1/2}$) | 0.600 | 0.588 | 0.672 | 0.62 | 0.58 |
| G1C (J/m$^2$) | 104.5 | 107.3 | 108.7 | 90.7 | 85.7 |

TABLE 3

| | Comparative Ex. 10 | Ex. 11 | Ex. 12 | Ex. 13 | Comparative Ex. 14 |
|---|---|---|---|---|---|
| Components | | | | | |
| Cationic composition CC | 95 | 94.3 | 93.6 | 92.95 | 92.2 |
| UVI6976 | 5.0 | 3.7 | 2.5 | 1.23 | |
| Esacure1064 | | 2.0 | 3.9 | 5.82 | 7.8 |
| Xa (%) | 0 | 35 | 61 | 83 | 100 |
| Total weight % | 100 | 100 | 100 | 100 | 100 |
| Viscosity at 30° C., upon storage at 65° C. (mPa · s) | | | | | |
| 0 days | 32 | 33 | 31 | 31 | 33 |
| 7 days | solid | 768 | 55 | 47 | 43 |

TABLE 3-continued

|  | Comparative Ex. 10 | Ex. 11 | Ex. 12 | Ex. 13 | Comparative Ex. 14 |
|---|---|---|---|---|---|
| Thermal stability at 65° C. (mPa · s/h) | >60 | 4.375 | 0.143 | 0.095 | 0.060 |
| Calculated Thermal stability at 65° C. - T.S. calc. (mPa · s/h) | / | 39 | 23.4 | 10.2 | / |
| Storage period (h) | 168 | 168 | 168 | 168 | 168 |
| Mechanical properties of cured specimens |  |  |  |  |  |
| Flexural Modulus (MPa) | 2822 | 2222 | 2193 | / | 1185 |
| K1C (MPa · m$^{1/2}$) | 0.85 | 0.541 | 0.591 | / | 0.401 |
| G1C (J/m$^2$) | 101 | 111 | 134 | / | 104 |

On tables 2 and 3, a compromise of good mechanical performances and thermal stability is achieved when Xa>50.

TABLE 3A

|  | Comparative Ex. A | Ex. 2A | Ex. 3A | Comparative Ex. 4 |
|---|---|---|---|---|
| Components |  |  |  |  |
| Cationic composition CC | 98.6 | 98.2 | 97.6 | 96.6 |
| Rhodorsil 2074 | 1.4 | 1.0 | 0.4 |  |
| Esacure1064 |  | 0.8 | 2 | 3.4 |
| Xa (%) | 0 | 28.5 | 71.5 | 100 |
| Total weight % | 100 | 100 | 100 | 100 |
| Viscosity at 30° C., upon storage at 65° C. (mPa · s) |  |  |  |  |
| 0 0 hour | 33.6 | 37.5 | 33 | 33.9 |
| 19 hours | / | 10000 | 1040 | / |
| Thermal stability at 65° C. (mPa · s/h) | >1000 | 526 | 55 | 0.029 |
| Calculated Thermal stability at 65° C. - T.S. calc. (mPa · s/h) | / | 715 | 285 | / |
| Storage period (h) | 8 | 19 | 19 | 144 |

Series 2: Hybrid Cationic/Free Radical Compositions

TABLE 4

|  | Comparative Ex. 15 | Ex. 16 | Ex. 17 | Ex. 18 | Ex. 19 | Ex. 20 | Comparative Ex. 21 |
|---|---|---|---|---|---|---|---|
| Components |  |  |  |  |  |  |  |
| Uvacure 1500 | 52.0 | 52.0 | 52.0 | 52.0 | 52.0 | 52.0 | 52.0 |
| DER332 | 5.0 | 5.0 | 5.0 | 5.0 | 5.0 | 5.0 | 5.0 |
| SR399 | 3.0 | 3.0 | 3.0 | 3.0 | 3.0 | 3.0 | 3.0 |
| SR499 | 15.0 | 15.0 | 15.0 | 15.0 | 15.0 | 15.0 | 15.0 |
| Arcol LG650 | 20.0 | 20.0 | 20.0 | 20.0 | 20.0 | 20.0 | 20.0 |
| Irgacure 184 | 2.0 | 2.0 | 2.0 | 2.0 | 2.0 | 2.0 | 2.0 |
| UVI-6976 | 3.0 | 2.6 | 2.0 | 1.5 | 0.8 | 0.3 |  |
| UVI-6992 |  | 0.4 | 1.0 | 1.5 | 2.2 | 2.7 | 3.0 |
| Total weight % | 100 | 100 | 100 | 100 | 100 | 100 | 100 |
| Xa (%) | 0 | 13 | 33 | 50 | 74 | 90 | 100 |
| Photosensitivity |  |  |  |  |  |  |  |
| E4 (mJ/cm$^2$) | 19.70 | 23.70 | / | 24.40 | / | / | 29.8 |
| Viscosity at 30° C., upon storage at 65° C. (mPa · s) |  |  |  |  |  |  |  |
| 0 days | 152 | 151 | 150 | 150 | 149 | 148 | 151 |
| 40 days | 2470 | 888 | 514 | 344 | 316 | 277 | 277 |
| Thermal stability at 65° C. (mPa · s/h) | 2.41 | 0.76 | 0.38 | 0.20 | 0.22 | 0.13 | 0.13 |
| Calculated Thermal stability at 65° C. - T.S. calc. (mPa · s/h) | / | 2.11 | 1.66 | 1.27 | 0.72 | 0.36 | / |
| Storage period (h) | 960 | 960 | 960 | 960 | 960 | 960 | 960 |

TABLE 4-continued

|  | Comparative Ex. 15 | Ex. 16 | Ex. 17 | Ex. 18 | Ex. 19 | Ex. 20 | Comparative Ex. 21 |
|---|---|---|---|---|---|---|---|
| Mechanical properties of cured specimens |  |  |  |  |  |  |  |
| Flexural Modulus (MPa) | 2828 | 2721 | / | 2747 | / | / | 891 |
| K1C (MPa·m$^{1/2}$) | 1.04 | 1.00 | / | 0.79 | / | / | 0.39 |
| G1C (J/m$^2$) | 324 | 312 | / | 191 | / | / | 507 |

TABLE 5

|  | Comparative Ex. 22 | Ex. 23 | Ex. 24 | Ex. 25 | Ex. 26 | Ex. 27 | Comparative Ex. 28 |
|---|---|---|---|---|---|---|---|
| Components |  |  |  |  |  |  |  |
| Uvacure 1500 | 52.0 | 51.8 | 51.7 | 51.1 | 51.0 | 50.9 | 50.4 |
| DER332 | 5.0 | 5.0 | 5.0 | 4.9 | 4.9 | 4.9 | 4.8 |
| SR399 | 3.0 | 3.0 | 3.0 | 3.0 | 2.9 | 2.9 | 2.9 |
| SR499 | 15.0 | 15.0 | 14.9 | 14.8 | 14.7 | 14.7 | 14.5 |
| Arcol LG650 | 20.0 | 19.9 | 19.9 | 19.7 | 19.6 | 19.6 | 19.4 |
| Irgacure 184 | 2.0 | 2.0 | 2.0 | 2.0 | 2.0 | 2.0 | 1.9 |
| UVI-6976 | 3.0 | 2.7 | 2.3 | 1.5 | 1.2 | 1.0 |  |
| UVI-6992 |  | 0.7 | 1.2 | 3.1 | 3.6 | 4.0 | 6.0 |
| Total weight % | 100 | 100 | 100 | 100 | 100 | 100 | 100 |
| Xa (%) | 0 | 20 | 34 | 67 | 74 | 80 | 100 |
| Photosensitivity |  |  |  |  |  |  |  |
| E4 (mJ/cm$^2$) | 19.70 | 23.60 | 27.0 | 29.50 | / | / | 33.1 |
| Viscosity at 30° C., upon storage at 65° C. (mPa·s) |  |  |  |  |  |  |  |
| 0 days | 150 | 147.5 | 145 | 145 | 142.5 | 140 | 137.5 |
| 21 days | 1837 | 380 | 272 | 238 | 245 | 240 | 255 |
| Thermal stability at 65° C. (mPa·s/h) | 3.35 | 0.46 | 0.25 | 0.18 | 0.20 | 0.20 | 0.23 |
| Calculated Thermal stability at 65° C. - T.S. calc. (mPa·s/h) | / | 3.55 | 2.28 | 1.26 | 1.04 | 0.85 | / |
| Storage period (h) | 504 | 504 | 504 | 504 | 504 | 504 | 504 |
| Mechanical properties of cured specimens |  |  |  |  |  |  |  |
| Flexural Modulus (MPa) | 2828 | 2763 | 2786 | 2872 | / | / | 2363 |
| K1C (MPa·m$^{1/2}$) | 1.04 | 1.00 | 0.93 | 0.92 | / | / | 0.86 |
| G1C (J/m$^2$) | 324 | 280 | 259 | 250 | / | / | 269 |

TABLE 6

|  | Comparative Ex. 29 | Ex. 30 | Ex. 31 | Ex. 32 | Comparative Ex. 33 |
|---|---|---|---|---|---|
| Components |  |  |  |  |  |
| Uvacure 1500 | 46.7 | 46.7 | 46.7 | 46.7 | 46.7 |
| OXT 101 | 9.2 | 9.2 | 9.2 | 9.2 | 9.2 |
| DER332 | 4.5 | 4.5 | 4.5 | 4.5 | 4.5 |
| SR399 | 3.1 | 3.1 | 3.1 | 3.1 | 3.1 |
| SR499 | 13.7 | 13.7 | 13.7 | 13.7 | 13.7 |
| Arcol LG650 | 18.0 | 18.0 | 18.0 | 18.0 | 18.0 |
| Irgacure 184 | 1.8 | 1.8 | 1.8 | 1.8 | 1.8 |
| UVI-6976 | 3.0 | 2.3 | 1.5 | 0.8 | 0 |
| UVI-6992 | 0 | 0.75 | 1.5 | 2.3 | 3.0 |
| Xa | 0 | 25 | 50 | 75 | 100 |
| Photosensitivity |  |  |  |  |  |
| E4 (mJ/cm$^2$) | 24.80 |  | 29.80 | 29.80 | / |
| Viscosity at 30° C., upon storage at 65° C. (mPa·s) |  |  |  |  |  |
| 0 days | 109 | 108 | 114 | 110 | 115 |
| 34 days | 842 | 296 | 145 | 122 | 121 |
| Thermal stability at 65° C. (mPa·s/h) | 0.90 | 0.23 | 0.038 | 0.015 | 0.007 |

TABLE 6-continued

| | Comparative Ex. 29 | Ex. 30 | Ex. 31 | Ex. 32 | Comparative Ex. 33 |
|---|---|---|---|---|---|
| Calculated Thermal stability at 65° C. - T.S. calc. (mPa · s/h) | / | 0.68 | 0.45 | 0.23 | / |
| Storage period (h) | 816 | 816 | 816 | 816 | 816 |
| Mechanical properties of cured specimens | | | | | |
| Flexural Modulus (MPa) | 2607 | / | 2507 | 2122 | / |
| K1C (MPa · m$^{1/2}$) | 0.95 | / | 0.98 | 0.98 | / |
| G1C (J/m$^2$) | 292 | / | 321 | 380 | / |

TABLE 7

| | Comparative Ex. 34 | Ex. 35 | Ex. 36 | Ex. 37 | Comparative Ex. 38 |
|---|---|---|---|---|---|
| Components | | | | | |
| Epalloy 5000 | 44.4 | 44.4 | 44.4 | 44.4 | 44.4 |
| Erisys GE30 | 5.0 | 5.0 | 5.0 | 5.0 | 5.0 |
| TMPO | 10.0 | 10.0 | 10.0 | 10.0 | 10.0 |
| SR833s | 14.0 | 14.0 | 14.0 | 14.0 | 14.0 |
| SR499 | 17.0 | 17.0 | 17.0 | 17.0 | 17.0 |
| Albidur EP2240 | 5.0 | 5.0 | 5.0 | 5.0 | 5.0 |
| Tego Rad 2100 | 0.1 | 0.1 | 0.1 | 0.1 | 0.1 |
| Irgacure 184 | 1.0 | 1.0 | 1.0 | 1.0 | 1.0 |
| UVI6976 | 3.5 | 2.6 | 1.8 | 0.9 | |
| Esacure 1064 | | 0.9 | 1.8 | 2.6 | 3.5 |
| Xa (%) | 0 | 25 | 50 | 75 | 100 |
| Photosensitivity | | | | | |
| E4 (mJ/cm$^2$) | 24.60 | / | 21.0 | / | 24.8 |
| Viscosity at 30° C., upon storage at 65° C. (mPa · s) | | | | | |
| 0 days | 169 | 169 | 172 | 170 | 168 |
| 19 days | 190 | 185 | 185 | 182 | 180 |
| Thermal stability at 65° C. (mPa · s/h) | 0.046 | 0.035 | 0.028 | 0.026 | 0.026 |
| Calculated Thermal stability at 65° C. - T.S. calc, (mPa · s/h) | / | 0.041 | 0.036 | 0.031 | / |
| Storage period (h) | 456 | 456 | 456 | 456 | 456 |
| Mechanical properties of cured specimens | | | | | |
| Flexural Modulus (MPa) | 1950 | / | 1876 | / | 1966 |
| K1C (MPa · m$^{1/2}$) | 1.28 | / | 1.42 | / | 1.52 |
| G1C (J/m$^2$) | 708 | / | 915 | / | 990 |

Series 3/Improvement of Green Strength in Hybrid Compositions

In a particular embodiment, it has been observed that green strength at 10 min can be increased by 180% by using a cationic photoinitiator mixture of the invention.

TABLE 8

| | Comparative Ex. 39 | Ex. 40 | Comparative Ex. 41 | Ex. 42 |
|---|---|---|---|---|
| Components | | | | |
| Epalloy 5000 | 52.9 | 52.62 | 48.9 | 48.7 |
| OXT 101 | 15 | 14.93 | 15 | 14.93 |
| CN 2301 | 5 | 4.98 | 5 | 4.98 |
| SR 833S | 20.1 | 20 | 20.1 | 20 |
| Albidur EP2240 | | | 4 | 3.97 |
| Irgacure 184 | 2 | 1.99 | 2 | 1.99 |
| UVI 6976 | | 0.5 | | 0.5 |
| Esacure 1064 | 5 | 4.98 | 5 | 4.98 |
| Total weight % | 100 | 100 | 100 | 100 |
| Xa | 100 | 90.9 | 100 | 90.9 |
| Mechanical properties of cured specimens | | | | |
| Green Flexural modulus @ 10 min (MPa) | 327 | 623 | 354 | 638 |

Series 4/Improvement of Mechanical Properties (Impact Resistance) in Hybrid Compositions

TABLE 9

| | Comparative Ex. 43 | Ex. 44 |
|---|---|---|
| Components | | |
| Epalloy 5000 | 49.5 | 49.25 |
| Erisys GE 30 | 14.02 | 13.95 |
| SR833 S | 18.8 | 18.71 |
| CN2301 | 4.68 | 4.66 |
| Nanostrength AFX E21 | 6 | 5.97 |
| Irgacure 184 | 2.0 | 1.99 |
| UVI-6976 | 5.0 | 4.98 |
| UVI-6992 | | 0.5 |
| Total weight % | 100 | 100 |
| Xa (%) | 0 | 20 |
| Photosensitivity | | |
| E4 (mJ/cm$^2$) | 56.37 | 56.37 |
| Mechanical properties of cured specimens | | |
| Flexural Modulus (MPa) | 2196 | 1968 |
| K1C (MPa · m$^{1/2}$) | 1.333 | 1.517 |
| G1C (J/m$^2$) | 720.4 | 944.1 |

Series 5/Photocurable Compositions Suitable for a Jet Printing Process

TABLE 10

| Components | Comparative Ex. 45 | Comparative Ex. 46 | Comparative Ex. 47 | Comparative Ex. 48 | Ex. 49 | Ex. 50 |
|---|---|---|---|---|---|---|
| UV 1500 | 50 | 51.5 | 50 | 47 | 50 | 48.5 |
| UVR 6000 | 45 | 46 | 45 | 43 | 45 | 44 |
| UVI 6976 | 5 | 2.5 | | | 2.5 | 2.5 |
| UVI 6992 | | | 5 | 10 | 2.5 | 5 |
| Total weight % | 100 | 100 | 100 | 100 | 100 | 100 |
| Time to surface cure (seconds) | 40 | 50 | 75 | 40 | 25 | 25 |

Relative cure speed of these resins has been estimated using a tack test based on the following methodology.

0.5 ml of resin is placed in a 55 mm diameter aluminium dish and exposed to UV (10 secs, 400 W Hg Lamp), at a distance of 12 inches.

The time after the start of UV exposure at which the surface is no longer tacky, judged by observing the adherence of a cotton wool bud to the surface is recorded. Times above 240 seconds were not recorded.

Table 10 demonstrates the effect of concentration and type of cationic photoinitiator on photocure speed. As is evident Comparative Examples 45 and 46 present only a slight difference in cure speed. For Comparative Examples 47 and 48 which use the sulfonium hexafluorophosphate UVI 6992 the concentration dependency on cure speed is high. 10 wt.-% of cationic photoinitiator (A) (UVI 6992) [Example 48] present in similar cure speed as 5 wt.-% of photoinitiator (B) (UVI 6976) [Example 45]. However, Examples 49 and 50 which present photocurable compositions according to the present invention comprising a mixture of cations photoinitiator (A) (UVI 6992) and a cationic photoinitiator (B) (UVI 6976) present a higher cure speed than either of the cationic photoinitiators (A) and (B) separately.

Stability of the Photocurable Composition:

With Examples 49 and 50, particularly, once the conditions for stable jetting were obtained at 70° C., reproducible jetting could be commenced readily for long duration, without clogging of the jets.

Formulations 49 and 50 comprising both UVI6976 and UVI6992 were tested for jettability:

Jettability requirements are:
Viscosity at jetting temperature of 1-30 mPas
Typical temperature used in printhead reservoir: 60-70° C.
Surface tension: <45 dynes per cm²
Suitable printheads are: Spectra Novajet.

Preparation of Jetted Samples:

Composition 49 was jetted using a 50 mm single nozzle jet device MJ-SF-01-50 mounted in a Jetlab™ (Microfab Technologies Inc, Plano, Tex.), with the reservoir held at 70° C. Peak voltage and rise, dwell and fall times were adjusted until stable jetting, without satellites, was obtained [below]. The mass of each droplet was measured by weighing the amount of fluid dispensed in a known time, and the droplet size was deducted from the mass measurement. The size of a single droplet deposited on a glass slide was measured using a calibrated graticule in a microscope.

Viscosity/mPa·s of the Composition According to Example 49

| | |
|---|---|
| at 25° C. | 69 mPa · s |
| at 70° C. | 8 mPa · s |

Ink Jet Pulse Parameters at 70° C.

| | |
|---|---|
| Rise&Fall [µs] | 5 |
| Dwell [µs] | 30 |
| Dwell [V] | 40 |
| Temp [° C.] | 70 |
| Freq [Hz] | 4000 |
| Droplet Mass [ng] | 138 |
| Deposited Droplet Diameter [µm] | 130 |

Example of the Jet Printing Process According to the Present Invention—Production of 2 Layer Samples The samples were deposited on an aluminium sheet, using the single piezoelectric jet printer head MJ-SF-01-50 from Microfab Technologies Inc, Plano, Tex., USA.

| | |
|---|---|
| Length of deposit | 10 to 15 millimeter |
| Width of deposit | 300 +/− 50 micrometer |
| Thickness: | 50 micrometer or more |

The printhead was heated to 70° C. and jetting was done using the following parameters:
printhead scan rate: 20 mm/second
drop density: 150 droplets/mm with a line space of 0.25 mm Two overlapping lines (1 cm) of droplets were deposited with a line space of 0.25 mm.

The jetted line was UV cured under a 4 W UVA lamp, with a curing energy of 120 mJ/cm².

For the two-layer deposit, a second layer was deposited onto the cured first layer and
then the deposit was cured under the same conditions.

A hard, scratch resistant deposit was obtained with very good overlap and merging of droplets.

The invention claimed is:

1. Photoinitiator composition comprising
   a) at least one cationic photoinitiator (A) selected from the group consisting of sulfonium salts wherein the anion is a fluorophosphate defined by the following formula (I):

   $$PF_nR^x{}_{6-n}{}^\ominus \qquad (I)$$

with n=an integer from 1 to 6 and
   $R^x$=substituted or unsubstituted $C_{1-6}$-alkyl or substituted or unsubstituted aryl or heteroaryl; and
   b) at least one cationic photoinitiator (B) which is different from (A) and is selected from at least one onium salt having a structure according to the following formula (VII)

   $$[R^1{}_aR^2{}_bR^3{}_cR^4{}_dE]^+[MX_{n+1}]^- \qquad (VII)$$

wherein
   E represents S, P, O, I or N≡N,
   $R^1$, $R^2$, $R^3$ and $R^4$ represent individually the same or different organic group selected from substituted or unsubstituted $C_{6-18}$ aryl;
   a, b, c, and d independently represent an integer from 0 to 3, and provided that a+b+c+d is 3 if E=S, 4 if E=P, 3 if E=O, 2 if E=I and 1 if E=N≡N;
   M represents a metal or metalloid selected from the group consisting of B, P, As Sb, Fe, Sn, Bi, Al;
   X represents F, Cl, Br, a substituted or unsubstituted aryl or heteroaryl group or mixtures thereof and;
   n is the valence number of M
   with the proviso that the onium salt is not a sulfonium salt wherein the anion is a fluorophosphate defined by the following formula (I):

   $$PF_nR^x{}_{6-n}{}^\ominus \qquad (I)$$

with n=1 to 6 and
   $R^x$=substituted or unsubstituted $C_{1-6}$-alkyl or substituted or unsubstituted aryl or heteroaryl and characterised in that the weight ratio of (A) to (B) is higher than 0.1.

2. Photoinitiator composition according to claim 1 characterised in that $R^1$, $R^2$, $R^3$ and $R^4$ represent individually the same or different organic group selected from phenyl, naphthyl, anthryl or phenanthryl, or substituted $C_{6-18}$ aryl which are substituted with one or more radicals selected from the group consisting of substituted or unsubstituted $C_{1-12}$-alkyl, $C_{1-6}$-alkoxy, $C_{1-6}$-alkylthio, halogen or arylthio and mixture thereof.

3. Photoinitiator composition according to claim 1 characterised in that the cationic photoinitiator (B) is selected from the group consisting of iodonium salts and hexafluoroantimonate salts.

4. Photoinitiator composition according to claim 1 characterised in that the weight ratio of (A) to (B) is higher than 0.2.

5. Photoinitiator composition according to claim 1 characterised in that the weight ratio of (A) to (B) is between 0.1 and 15.

6. Photoinitiator composition according to claim 1 characterised in that cationic photoinitiator (A) is represented by the following formula (III)

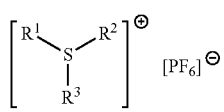
(III)

wherein $R^1$, $R^2$ and $R^3$ are each independently of one another $C_{6-18}$ aryl that is unsubstituted or substituted.

7. Photoinitiator composition according to claim 1 characterised in that cationic photoinitiator (B) is represented by the following formula (VIII)

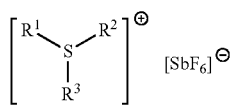
(VIII)

wherein $R^1$, $R^2$ and $R^3$ are each independently of one another $C_{6-18}$ aryl that is unsubstituted or substituted.

8. Photoinitiator composition according to claim 1 characterised in that the cationic photoinitiator (A) is represented by a mixture comprising

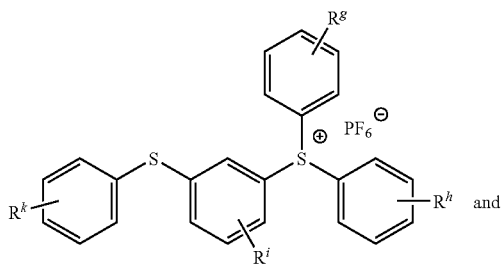
(IV)

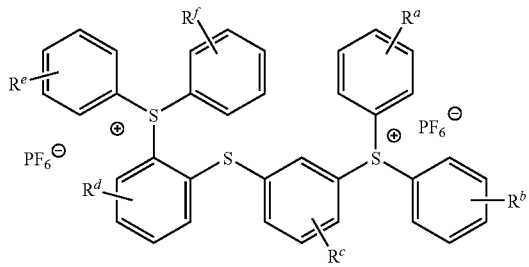
(VI)

wherein $R^a$, $R^b$, $R^c$, $R^d$, $R^e$, $R^f$, $R^g$, $R^h$, $R^i$ and $R^k$ are independently of one another H, —$OCH_3$, —$OCH_2CH_3$, methyl, ethyl, i-propyl, —$CH_2CH_2OH$, —$CH_2CH_2SH$.

9. Photoinitiator composition according to claim 1 characterised in that the cationic photoinitiator (B) is represented by a mixture comprising

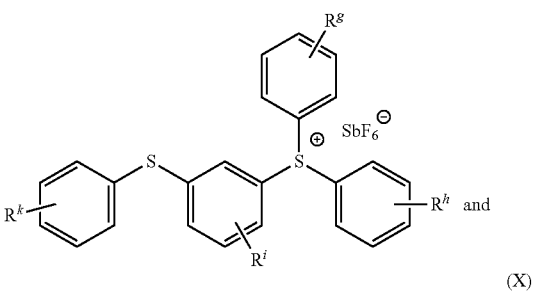
(IX)

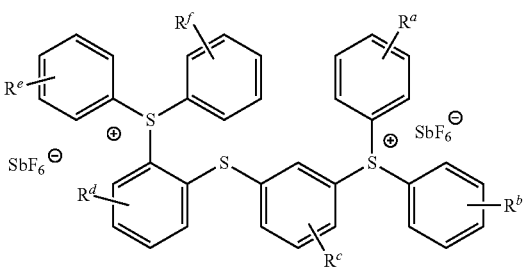
(X)

wherein $R^a$, $R^b$, $R^c$, $R^d$, $R^e$, $R^f$, $R^g$, $R^h$, $R^i$ and $R^k$ are independently of one another H, —$OCH_3$, —$OCH_2CH_3$, methyl, ethyl, i-propyl, —$CH_2CH_2OH$, —$CH_2CH_2SH$.

10. Photoinitiator composition according to claim 1 characterised in that the cationic photoinitiator (B) comprises at least one iodonium salt selected from the group consisting of (4-methylphenyl)(4-(2-methylpropyl)phenyl) iodonium hexafluorophosphate, bis (4-methylphenyl) iodonium hexafluorophosphate, bis(dodecylphenyl) iodonium hexafluorophosphate, bis(4-hexylphenyl) iodonium hexafluoroantimonate; bis(4-hexylphenyl) iodonium hexafluorophosphate; (4-hexylphenyl)phenyliodonium hexafluoroantimonate; (4-hexylphenyl)phenyliodonium hexafluorophosphate; bis(4-octylphenyl) iodonium hexafluoroantimonate; (4-sec-butylphenyl)-(4'-methylphenyl)iodonium hexafluorophosphate; (4-iso-proylphenyl)-(4'-methylphenyl)iodonium hexafluorophosphate; [4-(2-hydroxytetradecyloxy)phenyl]phenyliodonium hexafluoroantimonate; [4-(2-hydroxydodecyloxy)phenyl]phenyl iodonium hexafluoroantimonate; bis(4-octylphenyl) iodonium hexafluorophosphate; (4-octylphenyl)phenyliodonium hexafluoroantimonate; (4-octylphenyl)phenyliodonium hexafluorophosphate; bis(4-decylphenyl) iodonium hexafluoroantimonate; bis(4-decylphenyl)iodonium hexafluorophosphate; (4-decylphenyl)phenyliodonium hexafluoroantimonate; (4-decylphenyl)phenyliodonium hexafluorophosphate; (4-octyloxyphenyl)phenyliodonium hexafluoroantimonate; (4-octyloxyphenyl)phenyliodonium hexafluorophosphate; (2-hydroxydodecyloxyphenyl)phenyliodonium hexafluoroantimonate; (2-hydroxydodecyloxyphenyl)phenyliodonium hexafluorophosphate; bis(4-hexylphenyl)iodonium tetrafluoroborate; (4-hexylphenyl)phenyliodonium tetrafluoroborate; bis(4-octylphenyl) tetrafluoroborate; (4-octylphenyl)phenyliodonium tetrafluoroborate; bis(4-decylphenyl)iodonium tetrafluoroborate; bis (4-(mixed $C_4$-$C_8$-alkyl)phenyl) iodonium hexafluoroantimonate; (4-decylphenyl)phenyliodonium tetrafluoroborate;

(4-octyloxyphenyl)phenyliodonium tetrafluoroborate; (2-hydroxydodecyloxyphenyl)phenyliodonium tetrafluoroborate; biphenylene iodonium tetrafluoroborate; biphenylene iodonium hexafluorophosphate; and biphenylene iodonium hexafluoroantimonate.

11. Photoinitiator composition according to claim 1 characterised in that the cationic photoinitiator (B) is an iodonium tetrakis(pentafluorophenyl)borate.

12. Photoinitiator composition according to claim 1 characterised in that it further comprises at least one free-radical photoinitiator and/or photosensitizer.

13. Photoinitiator composition according to claim 1 characterised in that it comprises at least one free-radical photoinitiator in an amount of 0.1 to 90 wt.-% based on the total amount of the composition.

14. Photoinitiator composition according to claim 1 characterised in that it comprises at least one photosensitizer in an amount of 0.1 to 90 wt.-% based on the total amount of the photoinitiator composition.

15. Photocurable composition comprising a photoinitiator composition according to claim 1.

16. Photocurable composition according to claim 15 characterised in that it comprises a cationically curable component.

17. Photocurable composition according to claim 16 characterised in that the cationically curable component is selected from epoxy compounds, oxetanes, tetrahydropyranes, lactones and mixtures thereof.

18. Photocurable composition according to claim 15 characterised in that the cationically curable component is present in an amount of 2 to 90% by weight, wherein the percent by weight is based on the total weight of the photocurable composition.

19. Photocurable composition according to claim 15 characterised in that it further comprises a radically curable component.

20. Photocurable composition according to claim 15 characterised in that the radically curable component is a (meth)acrylate.

21. Photocurable composition according to claim 15 characterised in that the radically curable component is present in an amount of 5 to 80% by weight, wherein the percent by weight is based on the total weight of the photocurable composition.

22. Photocurable composition according to claim 15 characterised in that it comprises the photoinitiator composition in an amount between 0.1 to 30% by weight, wherein the percent by weight is based on the total weight of the photocurable composition.

23. Photocurable composition according to claim 15 wherein the photocurable composition has a viscosity in the range of 5 mPa·s to 10 Pa·s, at 30° C.

24. Photocurable composition according to claim 15 characterised in that it further contains a toughening agent comprising one or more block copolymers having at least one block composed of methyl methacrylate.

25. A process for producing a three dimensional article comprising:
    (a) forming a first layer of the photocurable composition according to claim 15 on a surface;
    (b) exposing the layer imagewise to irradiation to form an imaged cross-section;
    (c) forming a second layer of the photocurable composition in the previously exposed imaged cross-section;
    (d) exposing the second layer from step (c) imagewise to irradiation to form an additional imaged cross-section; and
    (e) repeating steps (c) to (d) a sufficient number of times in order to built up the three-dimensional article.

26. A process for producing a three dimensional article by jet printing comprising the steps of:
    (a') applying droplets of the photocurable composition according to claim 15 at targeted locations on a substrate;
    (b') exposing the droplets to electromagnetic radiation to cure the droplets in the exposed areas;
    (c') repeating steps (a') and (b') a sufficient number of times in order to build tip the three dimensional article.

27. Process according to claim 26 characterised in that the substrate is selected from the group consisting of paper, textiles, tiles, printing plates, wall paper, plastic, powder, paste, a reactive resin which is liquid and an already partly cured resin which is liquid.

28. Process according to claim 26 characterised in that the photocurable composition is exposed to electromagnetic radiation pixel by pixel, line by line, layer by layer.

29. Process according to claim 26 characterised in that the electromagnetic radiation employed is UV light, microwave radiation or visible light.

30. Process according to claim 26 characterised in that the photocurable composition used in a subsequent step is different from the photocurable composition used in a former step.

* * * * *